United States Patent
Robichaud

(10) Patent No.: US 11,096,767 B2
(45) Date of Patent: Aug. 24, 2021

(54) METHOD AND SYSTEM FOR GENERATING A MODEL OF A SUBPERIOSTEAL DENTAL IMPLANT DEVICE AND CUSTOMIZED IMPLANT HEAD

(71) Applicant: Panthera Dental Inc., Québec (CA)

(72) Inventor: Jean Robichaud, St- Aubert (CA)

(73) Assignee: Panthera Dental Inc., Quebec (CA)

(*) Notice: Subject to any disclaimer, the term of this patent is extended or adjusted under 35 U.S.C. 154(b) by 455 days.

(21) Appl. No.: 16/003,392

(22) Filed: Jun. 8, 2018

(65) Prior Publication Data

US 2018/0289454 A1    Oct. 11, 2018

Related U.S. Application Data

(62) Division of application No. 15/544,843, filed as application No. PCT/CA2016/050711 on Jun. 17, 2016, now Pat. No. 10,149,745.
(Continued)

(51) Int. Cl.
*A61C 13/00* (2006.01)
*A61B 34/10* (2016.01)
(Continued)

(52) U.S. Cl.
CPC .......... *A61C 13/0004* (2013.01); *A61B 34/10* (2016.02); *A61C 8/0027* (2013.01);
(Continued)

(58) Field of Classification Search
CPC ... A61C 13/0004; A61C 8/0027; A61C 13/34; A61C 8/005; A61C 9/0053; A61B 34/10; A61B 2034/102; A61B 2034/105
See application file for complete search history.

(56) References Cited

U.S. PATENT DOCUMENTS 4,702,697 A * 10/1987  Linkow ............... A61C 8/0031
                                                     433/173
4,741,698 A    5/1988  Andrews
(Continued)

FOREIGN PATENT DOCUMENTS

DE          40 36 753 A1    5/1992
DE    10 2011 112 507 A1    3/2013
(Continued)

OTHER PUBLICATIONS

Extended European Search Report issued in European Patent Application No. 20158405.9 dated May 12, 2020.
(Continued)

*Primary Examiner* — Nicholas D Lucchesi
(74) *Attorney, Agent, or Firm* — Marshall, Gerstein & Borun LLP

(57) ABSTRACT

A method for generating a virtual model of a subperiosteal dental implant device. The method comprises: obtaining a virtual mouth model of a patient providing a three-dimensional representation of at least a section of a jaw bone of a patient, using a non-invasive modelling method; positioning at least one replacement tooth in relation to the section of the jaw bone defined by the virtual mouth model; positioning at least one implant head at a respective implant position; and designing and generating a virtual model of the subperiosteal dental implant device having a shape at least partially derived from a shape of the section of the jaw bone defined by the virtual mouth model and at least a portion of each one of the at least one implant head extending from the subperiosteal dental implant device at the respective implant position.

18 Claims, 12 Drawing Sheets

Related U.S. Application Data

(60) Provisional application No. 62/181,575, filed on Jun. 18, 2015.

(51) Int. Cl.
  *A61C 8/00* (2006.01)
  *A61C 13/34* (2006.01)
  *A61C 9/00* (2006.01)

(52) U.S. Cl.
  CPC .......... *A61C 8/0031* (2013.01); *A61C 13/34* (2013.01); *A61B 2034/102* (2016.02); *A61B 2034/105* (2016.02); *A61C 8/005* (2013.01); *A61C 9/0053* (2013.01); *H05K 999/99* (2013.01)

(56) References Cited

U.S. PATENT DOCUMENTS

| | | | | |
|---|---|---|---|---|
| 5,098,296 A * | 3/1992 | Cullen | ............... | A61C 8/0048 433/173 |
| 5,306,150 A * | 4/1994 | Gittleman | ............ | A61F 2/2803 433/173 |
| 5,419,701 A * | 5/1995 | Propper | ............... | A61C 8/0009 433/173 |
| 5,769,630 A * | 6/1998 | Hoffman | ............. | A61B 17/663 433/173 |
| 5,820,369 A * | 10/1998 | Kvarnstrom | ......... | A61B 17/663 433/7 |
| 5,873,721 A * | 2/1999 | Willoughby | ......... | A61C 8/0001 433/173 |
| 6,645,250 B2 | 11/2003 | Schulter | | |
| 8,206,152 B2 * | 6/2012 | Holzner | ................. | A61C 13/01 433/195 |
| 8,527,079 B2 * | 9/2013 | Kim | ..................... | A61C 9/0046 700/98 |
| 8,532,806 B1 * | 9/2013 | Masson | ................. | B33Y 50/00 700/98 |
| 9,519,991 B2 * | 12/2016 | Jesenko | ............... | A61B 5/1077 |
| 9,539,062 B2 * | 1/2017 | Rubbert | ............. | A61C 13/0004 |
| 9,642,685 B2 * | 5/2017 | Brodkin | ............... | A61C 9/0053 |
| 9,801,697 B2 * | 10/2017 | Rubbert | ............... | A61C 8/0036 |
| 9,877,800 B1 * | 1/2018 | Silverman | ............... | A61C 5/20 |
| 9,934,333 B2 * | 4/2018 | Fisker | .................... | G06F 30/00 |
| 2007/0154868 A1 * | 7/2007 | Scharlack | ........... | A61C 13/0004 433/215 |
| 2008/0057478 A1 * | 3/2008 | Choi | ....................... | A61B 6/466 433/215 |
| 2008/0305456 A1 * | 12/2008 | Rosen | .................. | A61C 8/0031 433/173 |
| 2009/0029316 A1 * | 1/2009 | Dunn | ................... | A61C 8/0081 433/173 |
| 2009/0111071 A1 * | 4/2009 | Yau | ....................... | A61C 8/005 433/173 |
| 2012/0065756 A1 | 3/2012 | Rubbert et al. | | |
| 2012/0239364 A1 | 9/2012 | Glor et al. | | |
| 2013/0056892 A1 * | 3/2013 | Johnson | ............. | A61C 13/0013 264/19 |
| 2013/0149668 A1 | 6/2013 | Chen et al. | | |
| 2013/0164707 A1 * | 6/2013 | Ali | ........................ | A61C 8/0031 433/173 |
| 2017/0312057 A1 * | 11/2017 | Cheng | ................ | A61C 13/0028 |
| 2018/0161129 A1 * | 6/2018 | Mommaerts | ......... | A61C 8/0031 |

FOREIGN PATENT DOCUMENTS

| | | |
|---|---|---|
| DE | 20 2015 001 579 U1 | 5/2015 |
| EP | 2 594 224 A1 | 5/2013 |
| GB | 0 770 696 A | 3/1957 |

OTHER PUBLICATIONS

Supplemental Partial European Search Report for Application No. 16810684, dated Jan. 18, 2019.
Stoler, "Helical CT Scanning for CAD/CAM Subperiosteal Implant Construction," J. Oral Implantol., 22(3-4):247-257 (1996).
International Search Report and Written Opinion for Application No. PCT/CA2016/050711, dated Sep. 13, 2016.
Supplemental European Search Report for Application No. 16810684, dated Apr. 29, 2019.

* cited by examiner

Medical imagery images

Optical scan 3d model of gypsum model

Optical scan 3D model of diagnostic wax-up

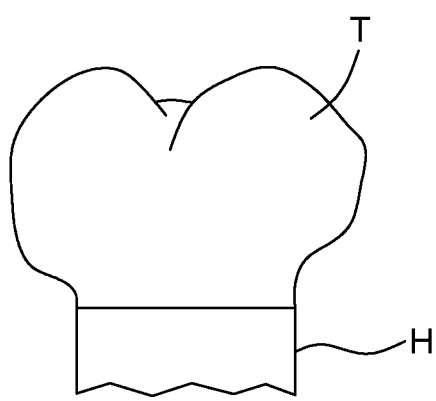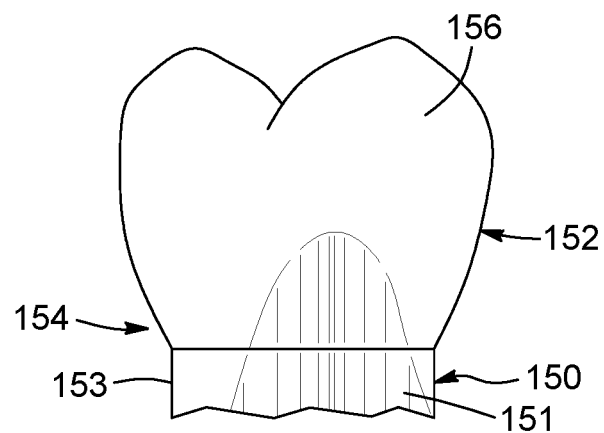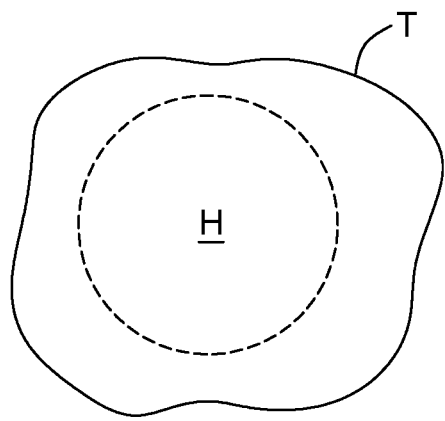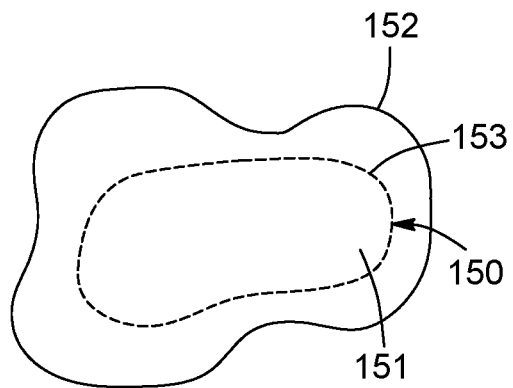
FIG. 17 (PRIOR ART)
FIG. 18
FIG. 19 (PRIOR ART)
FIG. 20

METHOD AND SYSTEM FOR GENERATING A MODEL OF A SUBPERIOSTEAL DENTAL IMPLANT DEVICE AND CUSTOMIZED IMPLANT HEAD

CROSS REFERENCE TO RELATED APPLICATION

This application is a divisional of U.S. patent application Ser. No. 15/544,843 filed on Jul. 19, 2017, now pending, which is a national phase entry of PCT patent application serial number PCT/CA2016/050711 filed Jun. 17, 2016, expired, and which claims priority under 35 U.S.C. § 119(e) of U.S. Provisional Patent Application No. 62/181,575 filed on Jun. 18, 2015, the specifications of each of which are hereby expressly incorporated by reference in their entireties herein.

TECHNICAL FIELD OF THE INVENTION

The present invention relates to the field of dental implant devices. More particularly, the present invention relates to a method and a system for generating a model of a subperiosteal dental implant device, to a dental implant system, and to a customized implant head for affixing a replacement tooth to a dental implant device, as well as to a method for designing the implant head.

BACKGROUND

Subperiosteal implants are implants being positioned below a patient's gum but on, or above, the jaw bone, rather than inside the bone. For example and without being limitative, this particular type of implant is commonly used for patients having a shallow jaw bone and which cannot or do not want to undergo a procedure to rebuild the jaw bone.

Subperiosteal implants typically include a metal framework and one or more replacement tooth. The metal framework is positioned over the jaw bone and attached thereon, underneath the gum tissue. The one or more replacement tooth is affixed to the metal framework. Known subperiosteal implants however tend to suffer from several drawbacks. For example, known subperiosteal implants are generic and selected from a library, i.e. they are not patient-specific and/or require the gum tissues to be chirurgically opened in order to acquire information regarding the shape of the jaw bone of the patient, which is undesirable.

Moreover, the metal framework of a subperiosteal dental implant and many other implants systems typically includes a base (or "implant head") for the one or more replacement tooth to be affixed thereon. Standard implant heads are commonly used on conventional dental implant devices. Standard implant heads also tend to suffer from several drawbacks. For example, they typically have a circular cylindrical shape to which a base of the one or more replacement tooth must be adapted to fit therewith, thereby departing from the natural dentition appearance of the patient.

In view of the above, there is a need for an improved system and method for manufacturing subperiosteal dental implants which would be able to overcome or at least minimize some of the above-discussed prior art concerns. Moreover, there is need for an improved implant head system for placing a replacement tooth thereon, which would also be able to overcome or at least minimize some of the above-discussed prior art concerns.

BRIEF SUMMARY OF THE INVENTION

According to a first general aspect, there is provided a method for generating a model of a subperiosteal dental implant device for a jaw, comprising:
a) obtaining, by a non-invasive modelling method, a patient's mouth model, the patient's mouth model providing a three-dimensional representation of the patient's dentition and jaw bone;
b) positioning at least one replacement tooth in relation to the patient's mouth model;
c) positioning at least one implant head, each one of the at least one implant head being aligned with a respective one of the at least one replacement tooth; and
d) defining and generating a model of the subperiosteal dental implant including at least a portion of the at least one implant head.

In an embodiment, the step (a) of obtaining the patient's mouth model comprises obtaining a three-dimensional model of the jaw bone via a medical imagery technique, such as a CT (computed tomography) scanning technology, for example, which provides information on the bone as well as of the existing teeth. Depending on the resolution of the CT scanning technology, the step (a) may further comprise obtaining a three-dimensional model of the patient's dentition via an intra-oral scanning technique, or by digitizing a physical model of the patient's dentition. The physical model can be obtained by taking an impression of a patient's maxillary and mandibular jaws with a dental impression material, thereby producing a mold from which a physical model the jaws can be made. The jaw bone model and the dentition model may thus be combined by matching the position of the dentition (i.e. the regions in each model corresponding to the patient's existing tooth or teeth), so as to provide the patient's mouth model representing the patient's dentition and jaw bone. The patient's mouth model may then be stored on a storage medium.

In these embodiments, the step (b) of positioning the at least one replacement tooth comprises: obtaining one or more digital tooth model from a library of tooth models, each digital tooth model representing one of said at least one replacement tooth; and positioning each digital tooth in relation to the patient's mouth model, for example using a CAD (computer-aided design) technology, to fill a toothless space in the patient's dentition.

In an embodiment, the step (a) may comprise: providing, on a storage medium, a 3D model of a diagnostic wax-up mounted on the jaw of a patient, said 3D model showing a jaw bone and at least one tooth model of the diagnostic wax-up; providing, on the storage medium, a 3D model of the jaw showing a gum line of the jaw (which can be obtained via an intra-oral scanning technique, or by digitizing a physical model of the jaw of the patient, similarly to the previously described embodiment); and superposing, by means of a processor, the two 3D models so as to obtain a three-dimensional model representing the patient's dentition, jaw bone and replacement tooth or teeth. Thus, in this particular embodiment, the step (b) of positioning the at least one replacement tooth is obtained through the above-mentioned superposing step.

According to another general aspect, there is provided a method of generating a model of a subperiosteal dental implant device for a jaw of a patient, comprising:
providing, on a storage medium, a 3D model of a diagnostic wax-up mounted on the jaw of a patient, said 3D model showing a jaw bone and at least one tooth model of the diagnostic wax-up;

providing, on the storage medium, a 3D model of the jaw of the patient showing a gum line;

superposing, by means of a processor, the two 3D models, to reveal a toothless space between the gum line and the jaw bone at a location of the at least one tooth model of the diagnostic wax-up, said space corresponding to a gum tissue of the jaw, so as to determine a position of at least one corresponding replacement tooth to be mounted on a frame of the subperiosteal dental implant device in relation to the jaw; and designing, generating and storing onto the storage medium, said model of the subperiosteal dental implant device.

In an embodiment, the replacement tooth/teeth intended to be mounted on the subperiosteal dental implant device is/are used as the model tooth/teeth of the diagnostic wax-up.

In an embodiment, the first 3D model showing the jaw bone and tooth model of the diagnostic wax-up can have some imperfections in the definition of the tooth model. In such an embodiment, the method may further comprise providing a 3D model of the diagnostic wax-up, on the storage medium, and the superposing step can further comprise superposing this third 3D model on the two other 3D models.

In an embodiment, the at least one tooth model (representing the at least one replacement tooth) are mounted on a base which is shaped and sized to mate with a section of the gum line of a patient's mouth, so that a patient can temporarily fit the diagnostic wax-up in his mouth.

According to another general aspect, there is provided a system for generating a model of a subperiosteal dental implant device, comprising:

a storage medium for storing a patient's mouth model providing a three-dimensional representation of the patient's dentition and jaw bone, the patient's mouth model having been obtained by a non-invasive modelling method;

a processor communicating with the storage medium for:
positioning at least one replacement tooth in relation to the patient's mouth model;
positioning at least one implant head aligned with a respective one or more of the at least one replacement tooth; and
designing and generating a model of the subperiosteal dental implant including the at least one implant head.

According to another general aspect, there is provided an implant head for affixing a replacement tooth to a dental implant device, the implant head being sized and shaped to conform to the shape of the replacement tooth.

According to another general aspect, there is provided a method for designing an implant head for affixing a replacement tooth to a dental implant device. The method comprises: obtaining a model of a section of a patient's jaw including the replacement tooth and a section of a gum tissue and a jaw bone underlying the replacement tooth; and designing a peripheral wall of the implant head by extending a peripheral wall of the replacement tooth model towards the section of the gum tissue and the jaw bone, the peripheral wall of the implant head being aligned with a base section of the peripheral wall of the replacement tooth model.

According to another general aspect, there is provided a method for modeling an implant head for affixing a replacement tooth to a dental implant device. The method comprises: obtaining a model of the dental implant device and of the replacement tooth positioned at a desired final position in relation to the dental implant device; and defining at least a portion of the implant head to extend from a frame of the dental implant device to a base of the replacement tooth, and further defining the implant head to match the contour of the base of the replacement tooth.

According to another general aspect, there is provided a dental implant system, comprising:
a dental implant device; and
one or more connector removably mountable to the dental implant device and configured to receive one or more replacement tooth, in order to connect said one or more replacement tooth with the dental implant device.

In an embodiment, the dental implant device comprises a frame to be mounted in a patient's mouth, the dental implant device further comprising one or more implant heads, each extending from the frame. Each implant head is adapted to receive one or more replacement tooth. According to an embodiment, the frame is adapted to be mounted on a jaw bone of a patient.

In an embodiment, the implant head has a socket which is threaded and adapted to receive a connector. The connector comprises a threaded end for mating with the socket of the implant head, and a connecting head opposite the threaded end, for connecting with the one or more replacement tooth. The one or more replacement tooth comprises an opening shaped to mate with the connecting head of the connector.

According to still another general aspect, there is provided a dental implant system, comprising:
a dental implant device including a frame to be mounted in a patient's mouth with a receiving portion of an implant head, the receiving portion extending from the frame; and
a head portion of the implant head, the head portion being securable to the receiving portion to receive a replacement tooth.

In an embodiment, the replacement tooth is a replacement tooth assembly including a plurality of adjacent teeth secured together.

In an embodiment, the frame is adapted to be mounted on a jaw bone of a patient. In a particular embodiment, the dental implant device is a subperiosteal dental implant.

In an embodiment, the receiving portion has a cavity defined therein configured to receive the head portion. In an embodiment, the head portion is cemented into the cavity. In an embodiment, the head portion comprises a threaded socket to be engaged by a connector. The connector comprises a threaded end for mating with the socket of the implant head, and a connecting head opposite the threaded end, for connecting with the replacement tooth. The replacement tooth comprises an opening shaped to mate with the connecting head of the connector.

According to another general aspect, there is provided a method for generating a virtual model of a subperiosteal dental implant device for a jaw of a patient having a gum tissue with a gum line. The method comprises the steps of:
obtaining a virtual mouth model of a patient using a non-invasive modelling method, the virtual mouth model of the patient providing a three-dimensional representation of at least a section of a jaw bone of the patient;
positioning at least one replacement tooth in relation to the section of the jaw bone defined by the virtual mouth model of the patient;
positioning at least one implant head at a respective implant position wherein each one of the at least one implant head is aligned with a respective one of the at least one replacement tooth; and designing and generating a virtual model of the subperiosteal dental implant device having a frame with a shape at least partially derived from a shape of the section of the jaw bone defined by the virtual mouth model of the patient and at least a portion of each one of the at least one implant head extending from the frame at the respective implant position.

In an embodiment, designing and generating the virtual model of the subperiosteal dental implant device further comprises at least partially conforming the shape of the frame to an external shape of the section of the jaw bone defined by the virtual mouth model of the patient.

In an embodiment, obtaining the virtual mouth model of the patient comprises acquiring a three-dimensional virtual model of the jaw of the patient using a medical imagery technique.

In an embodiment, acquiring the three-dimensional virtual model of the jaw of the patient using a medical imagery technique comprises: acquiring CT scan images of the section of the jaw bone of the patient through a computed tomography scan thereof; and generating the three-dimensional model of the section of the jaw bone using the CT scan images.

In an embodiment, obtaining the virtual mouth model of the patient comprises: providing a diagnostic wax-up comprising at least one tooth model; and positioning the diagnostic wax-up against a surface of the gum tissue of the patient at least partially covering the section of the jaw bone. The diagnostic wax-up is positioned against the surface of the gum tissue of the patient when acquiring the three-dimensional virtual model of the jaw bone of the patient using the medical imagery technique.

In an embodiment, obtaining the virtual mouth model of the patient further comprises obtaining an optical three-dimensional virtual model of the at least one tooth model of the diagnostic wax-up.

In an embodiment, the at least one tooth model is at least one radiopaque tooth model.

In an embodiment, obtaining the virtual mouth model of the patient comprises acquiring an optical three-dimensional virtual model of the jaw of the patient representing at least a section the gum line of the patient.

In an embodiment, acquiring the optical three-dimensional model of the jaw of the patient comprises performing one of an intra-oral scan of at least a portion of the mouth of the patient and an optical scan of a physical model of the jaw of the patient.

In an embodiment, the three-dimensional virtual model of the jaw of the patient defines at least one toothless space for positioning the at least one replacement tooth and positioning the at least one replacement tooth in relation to the section of the jaw bone defined by the virtual mouth model of the patient comprises: selecting at least one digital tooth model from a library of tooth models, each one of the at least one digital tooth model representing a respective one of the at least one replacement tooth; and positioning each one of the at least one digital tooth model in a corresponding one of the at least one toothless space defined in the three-dimensional virtual model of the jaw of the patient, using a computer-aided design technology.

In an embodiment, positioning the at least one replacement tooth in relation to the section of the jaw bone defined by the virtual mouth model of the patient comprises: superposing the three-dimensional virtual model of the jaw of the patient and the optical three-dimensional virtual model of the jaw of the patient, thereby generating a combined three-dimensional virtual model defining at least one toothless space for positioning the at least one replacement tooth; selecting at least one digital tooth model from a library of tooth models, each one of the at least one digital tooth model representing a respective one of the at least one replacement tooth; and positioning each one of the at least one digital tooth model in relation to the jaw bone of the patient, in a corresponding one of the at least one toothless space defined in the combined three-dimensional virtual model, using a computer-aided design technology.

In an embodiment, positioning the at least one replacement tooth in relation to the jaw bone defined by the virtual mouth model of the patient comprises: extracting a position of the at least one tooth model in relation to the section of the jaw bone of the patient from the virtual mouth model including the three-dimensional representation of the at least one tooth model; and positioning each one of the at least one replacement tooth in relation to the jaw bone of the patient at the position of a corresponding one of the at least one tooth model.

In an embodiment, positioning at least one replacement tooth in relation to the jaw bone defined by the virtual mouth model of the patient comprises: superposing the three-dimensional virtual model of the jaw of the patient and the optical three-dimensional virtual model of the at least one tooth model of the diagnostic wax-up, thereby generating a combined three-dimensional virtual model; extracting a position of the at least one tooth model in relation to the section of the jaw bone of the patient from the combined three-dimensional virtual model representing the at least one tooth model and the section of the jaw bone of the patient; and positioning each one of the at least one replacement tooth in relation to the jaw bone of the patient at the extracted position of a corresponding one of the at least one tooth model.

In an embodiment, positioning at least one replacement tooth in relation to the jaw bone defined by the virtual mouth model of the patient comprises: superposing the three-dimensional virtual model of the jaw of the patient and the optical three-dimensional virtual model of the jaw of the patient, thereby generating a combined three-dimensional virtual model; extracting a position of the at least one tooth model in relation to the jaw bone of the patient from the combined three-dimensional virtual model representing the at least one tooth model, the section of the gum line of the patient and the section of the jaw bone of the patient; and positioning each one of the at least one replacement tooth in relation to the jaw bone of the patient at the extracted position of a corresponding one of the at least one tooth model.

In an embodiment, positioning at least one replacement tooth in relation to the jaw bone defined by the virtual mouth model of the patient comprises: superposing the three-dimensional virtual model of the jaw of the patient, the optical three-dimensional virtual model of the at least one tooth model and the optical three-dimensional virtual model of the jaw of the patient, thereby generating a combined three-dimensional virtual model; extracting a position of the at least one tooth model from the combined three-dimensional virtual model representing the at least one tooth model, the section of the gum line of the patient and the section of the jaw bone of the patient; and positioning each one of the at least one replacement tooth in relation to the jaw bone of the patient at the extracted position of a corresponding one of the at least one tooth model.

In an embodiment, each one of the at least one replacement tooth comprises a peripheral wall with an irregular base section and the implant head comprises a body engageable with the respective one of the at least one replacement tooth, the body having a peripheral wall substantially matching a peripheral shape of the irregular base section of the peripheral wall of the respective one of the at least one replacement tooth at a junction thereof.

In an embodiment, deriving the shape of the frame comprises interconnecting a plurality of frame segments and substantially aligning at least one intersection of the frame segments with the respective implant position.

In accordance with another general aspect, there is provided a computer implemented method for generating a virtual model of a subperiosteal dental implant device having a frame for a jaw of a patient using a diagnostic wax-up including at least one tooth model engageable with a surface of a gum tissue of the patient. The computer implemented method comprises:
    storing on a storage medium a three-dimensional model of the diagnostic wax-up superposed to the surface of the gum tissue of the patient, said three-dimensional model representing at least a section of a jaw bone of the patient and the at least one tooth model of the diagnostic wax-up;
    storing on the storage medium an optical three-dimensional model of the jaw of the patient representing at least a section of a gum line of the gum tissue of the patient;
    superposing, by means of a processor, the three-dimensional model of the diagnostic wax-up superposed to the surface of the gum tissue of the patient and the optical three-dimensional model of the jaw of the patient and generating a combined three-dimensional virtual model, the combined three-dimensional virtual model defining a space between the gum line and the jaw bone of the patient substantially aligned with the at least one tooth model of the diagnostic wax-up corresponding to the gum tissue of the jaw of the patient;
    determining a position of at least one replacement tooth to be mounted on the frame of the subperiosteal dental implant device, the position corresponding substantially to a position of the at least one tooth model of the diagnostic wax-up in the combined three-dimensional virtual model;
    designing and generating the virtual model of the subperiosteal dental implant device including the frame and at least a portion of at least one implant head mounted to the frame, a shape of the frame being at least partially derived from an external shape of the section of the jaw bone of the combined three-dimensional virtual model and the at least portion of the at least one implant head being substantially aligned with a corresponding one of the at least one replacement tooth and extending in the gum tissue, and
    storing the generated model of the subperiosteal dental implant device onto the storage medium.

In an embodiment, the method further comprises storing an optical three-dimensional model of the diagnostic wax-up on the storage medium and superposing the three-dimensional models comprises superposing the three-dimensional model of the diagnostic wax-up mounted on the jaw of a patient, the optical three-dimensional model of the jaw of the patient and the optical three-dimensional model of the diagnostic wax-up to generate the combined three-dimensional virtual model.

In an embodiment, the at least one tooth model is at least one radiopaque tooth model.

In an embodiment, deriving the shape of the frame comprises substantially conforming a bone-facing surface of the frame to the external shape of the section of the jaw bone of the patient.

In an embodiment, deriving the shape of the frame comprises interconnecting a plurality of frame segments and substantially aligning at least one intersection of the frame segments with the position of the at least one replacement tooth.

In accordance with another general aspect, there is provided a system for generating a virtual model of a subperiosteal dental implant device for a jaw of a patient having a gum tissue with a gum line. The system comprises:
    a storage medium for storing a virtual mouth model of a patient providing a three-dimensional representation of at least a section of a jaw bone of the patient, the virtual mouth model of the patient being acquired using a non-invasive modelling method;
    a processor communicating with the storage for:
        positioning at least one replacement tooth in relation to the virtual mouth model of the patient;
        positioning at least one implant head at a respective implant position wherein each one of the at least one implant head is substantially aligned with a corresponding one of the at least one replacement tooth; and
        designing and generating the virtual model of the subperiosteal dental implant, the subperiosteal dental implant having a frame substantially conforming to at least a section of an external surface of the jaw bone represented in the virtual mouth model of the patient and at least a portion of each of the at least one implant head being mounted to the frame at the respective implant position.

In an embodiment, the virtual mouth model comprises a three-dimensional virtual model of the jaw of the patient acquired using a medical imagery technique.

In an embodiment, the three-dimensional virtual model of the jaw of the patient acquired using the medical imagery technique represents the section of the jaw bone and at least one tooth model of a diagnostic wax-up superposed to a surface of the gum tissue of the patient.

In an embodiment, the virtual mouth model comprises an optical three-dimensional virtual model of the diagnostic wax-up including the at least one tooth model.

In an embodiment, the at least one tooth model is at least one radiopaque tooth model.

In an embodiment, the virtual mouth model comprises an optical three-dimensional virtual model of the jaw of the patient representing the gum line of the patient.

In accordance with another general aspect, there is provided a subperiosteal dental implant device for receiving at least one replacement tooth of a patient. The subperiosteal dental implant device comprises a frame engageable to at least a section of a jaw bone of the patient, the frame at least partially conforming to an external shape of the section of the jaw bone of the patient; and an implant head configured to receive a corresponding one of the at least one replacement tooth, the implant head extending from the frame and at least a portion of the implant head being integral with the frame.

In an embodiment, the at least one replacement tooth comprises a plurality of adjacent teeth secured to one another.

In an embodiment, the implant head comprises a threaded socket engageable by a connector. The connector comprises a threaded end for mating with the threaded socket of the implant head and a connecting head opposite the threaded end for connecting with the corresponding one of the at least one replacement tooth.

In an embodiment, the subperiosteal dental implant device further comprises a positioning jig removably connectable between the subperiosteal dental implant device and at least one existing tooth of the patient. The positioning jig has a body with a tooth engaging feature engageable with the at least one existing tooth of the patient and a frame engaging feature removably engageable to the implant head.

In an embodiment, the frame has a bone-facing surface which substantially conforms to a section of the jaw bone of the patient to which the frame is superposed.

In an embodiment, the frame comprises a plurality of interconnected segments wherein at least some of the plurality of interconnected segments intersect with the implant head.

In an embodiment, the at least a portion of the implant head is mounted to the segments intersecting therewith.

In an embodiment, the corresponding one of the at least one replacement tooth comprises a peripheral wall with an irregular base section and the implant head comprises a body engageable with the corresponding one of the at least one replacement tooth, the body having a peripheral wall substantially matching a peripheral shape of the irregular base section of the peripheral wall of the replacement tooth at a junction thereof.

In accordance with another general aspect, there is provided a dental implant system for mounting at least one replacement tooth onto a jaw of a patient having at least one existing tooth. The dental implant system comprises a subperiosteal dental implant device having a frame superposable to a jaw bone of the jaw of the patient, the frame having a bone-facing surface at least partially conforming to an external shape of at least a section of the jaw bone of the patient; and a positioning jig having a jig body with a tooth engaging feature engageable with at least one of the at least one existing tooth of the patient and a frame engaging feature removably engageable with the frame of the subperiosteal dental implant device. The subperiosteal dental implant device is positioned in a single predetermined position with respect to the jaw bone of the patient when the tooth engaging feature of the positioning jig is engaged with the respective one of the at least one existing tooth of the patient, the frame engaging feature is engaged with the frame of the subperiosteal dental implant device, and the bone-facing surface of the frame of the subperiosteal dental implant device is superposed to the jaw bone of the patient.

In an embodiment, the at least one replacement tooth comprises a plurality of adjacent teeth secured to one another.

In an embodiment, the subperiosteal dental implant device further comprises at least a portion of an implant head configured to receive a corresponding one of the at least one replacement tooth, the at least a portion of the implant head being mounted to and extending from the frame.

In an embodiment the at least a portion of the implant head is integral with the frame.

In an embodiment, the frame engaging feature is removably securable to the at least a portion of the implant head.

In an embodiment, the implant head of the subperiosteal dental implant device comprises a threaded socket and the frame engaging feature is removably engageable with the threaded socket of the implant head.

In an embodiment, the implant head comprises a body engageable with the corresponding one of the at least one replacement tooth and the corresponding one of the at least one replacement tooth comprises a peripheral wall with an irregular base section. The body of the implant head has a peripheral wall substantially matching a peripheral shape of the irregular base section of the peripheral wall of the replacement tooth at a junction thereof.

In an embodiment, the tooth engaging feature of the positioning jig at least partially surrounds the respective one of the at least one existing tooth of the patient when engaged therewith.

In an embodiment the tooth engaging feature comprises a tooth facing surface, the tooth facing surface substantially conforming to at least a portion of an external surface of the respective one of the at least one existing tooth of the patient.

In accordance with another general aspect, there is provided a method for mounting a subperiosteal dental implant device to jaw bone of a patient. The method comprises:
  providing the above-described dental implant system;
  engaging the frame engaging feature of the positioning jig with the frame of the subperiosteal dental implant device;
  superposing the bone-facing surface of the frame to the jaw bone of the patient with the bone-facing surface substantially conforming to the jaw bone of the patient to which it is superposed;
  engaging the tooth engaging feature of the positioning jig with the respective one of the at least one existing tooth of the patient;
  securing the subperiosteal dental implant device to the jaw bone of the patient; and
  disengaging the tooth engaging feature of the positioning jig from the respective one of the at least one existing tooth of the patient and the frame engaging feature from the frame of the subperiosteal dental implant device and removing the positioning jig.

In accordance with another general aspect, there is provided a method for designing an implant head for affixing a replacement tooth to a jaw of a patient. The replacement tooth has a peripheral wall with an irregular base section and the implant head has a body with a peripheral wall. The method comprises: obtaining a tooth model of the replacement tooth, the tooth model including a peripheral shape of the peripheral wall in the irregular base section of the replacement tooth; determining a junction line between the irregular base section of the replacement tooth and the body of the implant head when engaged together using the tooth model; and designing the implant head with a peripheral shape of the peripheral wall of the body substantially matching the peripheral shape of the peripheral wall of the replacement tooth at the junction line, using the tooth model.

In an embodiment, the method further comprises: obtaining a model of at least a section of a gum line of a gum tissue of the jaw of the patient; positioning the replacement tooth and the implant head with respect to the gum line; and substantially aligning the junction line between the irregular base section of the replacement tooth and the implant head with the gum line.

In an embodiment, the model of the replacement tooth and the model of the gum line of the gum tissue are virtual models.

In an embodiment, designing the implant head further comprises virtually extending the peripheral wall of the tooth model in the irregular base section in a direction corresponding to the jaw of the patient when the replacement tooth is mounted thereto; determining a peripheral shape of the virtual extension of the peripheral wall of the tooth model at the junction line; and shaping the peripheral shape of the peripheral wall of the body to be in register with the peripheral wall of the tooth model at the junction line.

In an embodiment, designing the implant head further comprises designing at least a section of the body of the implant head to be contained in the jaw of the patient.

In accordance with another general aspect, there is provided an implant head for affixing a replacement tooth to a jaw of a patient. The replacement tooth has a peripheral wall with an irregular base section. The implant head comprises a body configured to at least partially extend through a gum tissue of the jaw of the patient and being engageable with the replacement tooth. The body has a peripheral wall substantially matching a peripheral shape of the irregular base section of the peripheral wall of the replacement tooth at a junction thereof.

In an embodiment, the peripheral shape of the irregular base section of the peripheral wall of the replacement tooth and the peripheral wall of the body of the implant head are in register at a junction thereof.

In an embodiment, the body of the implant head is custom-shaped and is at least partially derived from the peripheral shape of the irregular base section of the peripheral wall of the replacement tooth.

In an embodiment, the irregular base section is non-circular and non-ovoidal.

In an embodiment, the junction of the peripheral wall of the implant head with the irregular base section of the replacement tooth is located in a vicinity of a gum line of the gum tissue when the implant head and the replacement tooth are mounted to the jaw of the patient.

In accordance with another general aspect, there is provided a dental implant device comprising a frame engageable with a jaw bone of a patient; and the implant head as described above mounted to the frame and protruding therefrom.

In an embodiment, the implant head is integral with the dental implant device.

In an embodiment, the dental implant device comprises a subperiosteal dental implant device.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIGS. 14a, 14b, and 14c; are respectively a perspective view of a partial subperiosteal dental implant device in accordance with an embodiment including two receiving portions of implant heads; a perspective view of a head portion engageable with one of the receiving portions of implant heads of FIG. 14a; and a perspective view of two head portions engaged with the receiving portions of the implant heads of the partial subperiosteal dental implant device of FIG. 14a.

FIG. 17 is a schematic side elevation view of a conventional implant head for an implant device having a replacement tooth affixed thereto, in accordance with the prior art.

FIG. 18 is a schematic side elevation view of an implant head for an implant device having a replacement tooth affixed thereto, in accordance with an embodiment.

FIG. 19 is a schematic bottom plan view of the conventional implant head shown in FIG. 17.

FIG. 20 is a schematic bottom plan view of the implant head shown in FIG. 18.

DETAILED DESCRIPTION

In the following description, the same numerical references refer to similar elements. The embodiments, geometrical configurations, materials mentioned and/or dimensions shown in the figures or described in the present description are embodiments only, given solely for exemplification purposes.

Although the embodiments as illustrated in the accompanying drawings comprises particular steps of a method and although the embodiment of the system explained and illustrated herein include particular components, not all of these components and steps are essential and thus should not be taken in their restrictive sense, i.e. should not be taken as to limit the scope of the present invention. It is to be understood, as also apparent to a person skilled in the art, that other suitable components, and cooperation therebetween, as well as other suitable configurations can be used for the method and system, as will be briefly explained herein and as can be easily inferred herefrom, by a person skilled in the art, without departing from the scope of the invention.

Figure 1A:
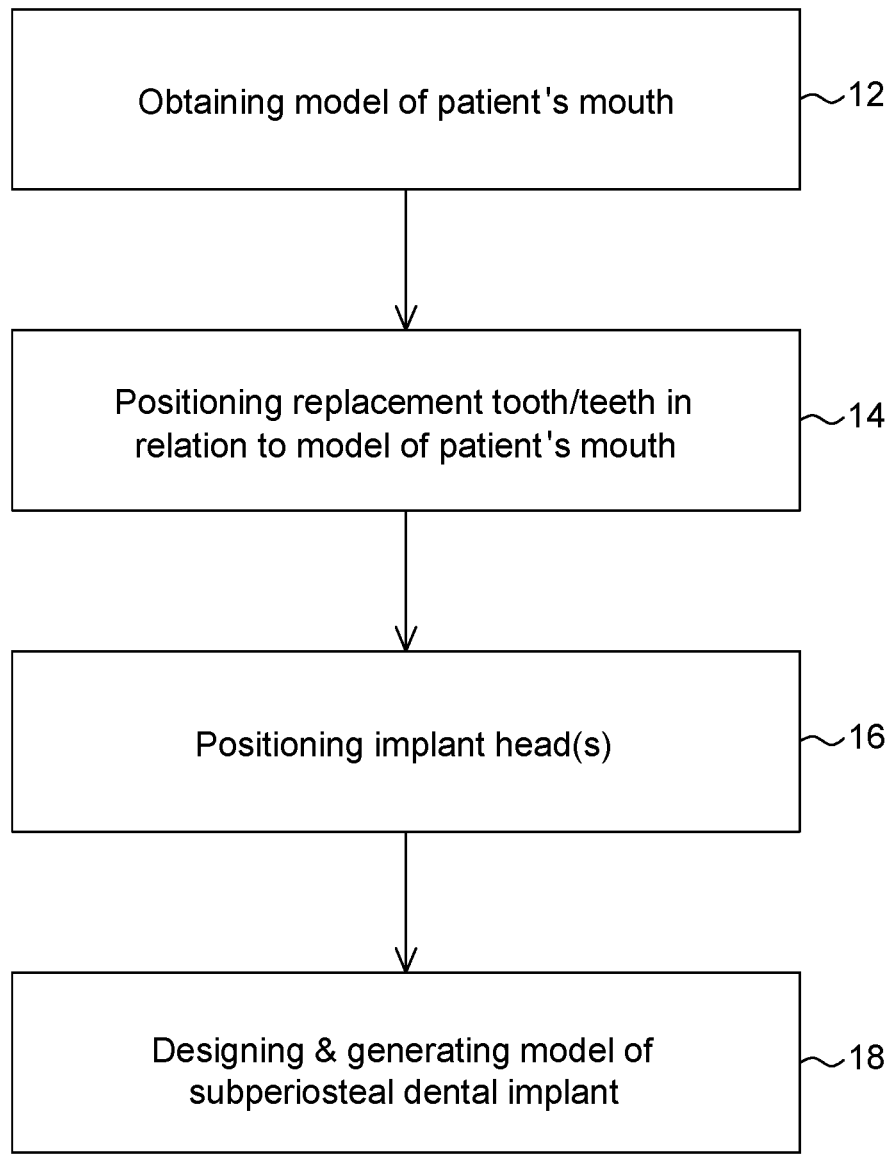
FIG. 1A is a bloc diagram showing steps of a process for generating a model of a subperiosteal dental implant device, according to an embodiment.

According to a broad embodiment and as illustrated in FIG. 1A, there is provided a method 10 for designing and generating a model of a subperiosteal dental implant device. The method comprises an initial step of obtaining at least a partial mouth model of a patient. In an embodiment, the mouth model includes at least a model of the jaw bone of the patient (step 12). In an embodiment where the patient is not toothless, the mouth model can also show existing tooth or teeth of the patient positioned above the jaw bone and at least one toothless space. In an embodiment, the mouth model of the patient is obtained using a non-invasive modelling method such as, without being limitative a medical imagery technique, an optical imaging techniques or a combination thereof. In an embodiment and without being limitative, the medical imagery technique can be computed tomography (CT) or a magnetic resonance imaging (MRI). The method can include the additional steps of positioning one or more replacement tooth in relation to the mouth or the mouth model of the patient (step 14) and positioning one or more implant head at a respective implant position wherein each implant head is in alignment with a respective one of the one or more replacement tooth (step 16). The method can also comprise the further step of designing and generating a model of the subperiosteal dental implant including at least a portion of each one of the one or more implant head (step 18).

In an embodiment, the mouth model including at least a section of the jaw bone can also include tooth models, which positions will eventually correspond to the position of the replacement tooth/teeth. Thus, the step of positioning one or more replacement tooth in relation to the mouth or the mouth model of the patient (step 14) can correspond to associating a replacement tooth to each one of the tooth models. For instance, a first mouth model can be acquired to design a diagnostic wax-up including one or more tooth model. Then, the diagnostic wax-up can be positioned in the patient's mouth and a medical imaging method (e.g. a CT scan, a magnetic resonance imaging (MRI), or the like) providing medical imagery images of the patient's mouth including the diagnostic wax-up can be performed. Medical imaging data includes information about the patient's jaw bone and the tooth models. Thus, a position of the replacement tooth/teeth can then be determined based of the position of the tooth models in relation to the jaw bone.

In an embodiment, the mouth model of the patient is a virtual model provided in the form of data on a storage medium. In the course of the present document, the term storage medium is used to refer to non-transient and computer-readable mediums, such as, for example and without being limitative: a temporary storage unit such as a random-access memory (RAM) or dynamic RAM; a permanent storage such as a hard disk; an optical storage device, such as a CD or DVD (rewritable or write once/read only); a flash memory; and/or the like.

In the course of the present document, even though the models are referred to as being a model of a jaw, a jaw bone or a gum line of a patient, one skilled in the art will appreciated that the model can include only a section of the patient's jaw, jaw bone or gum line. Furthermore, the models can be a model of a patient's mandible, maxillary or both, or only a section thereof.

Modelisation and Fabrication of a Subperiosteal Dental Implant Device

Figure 1B:
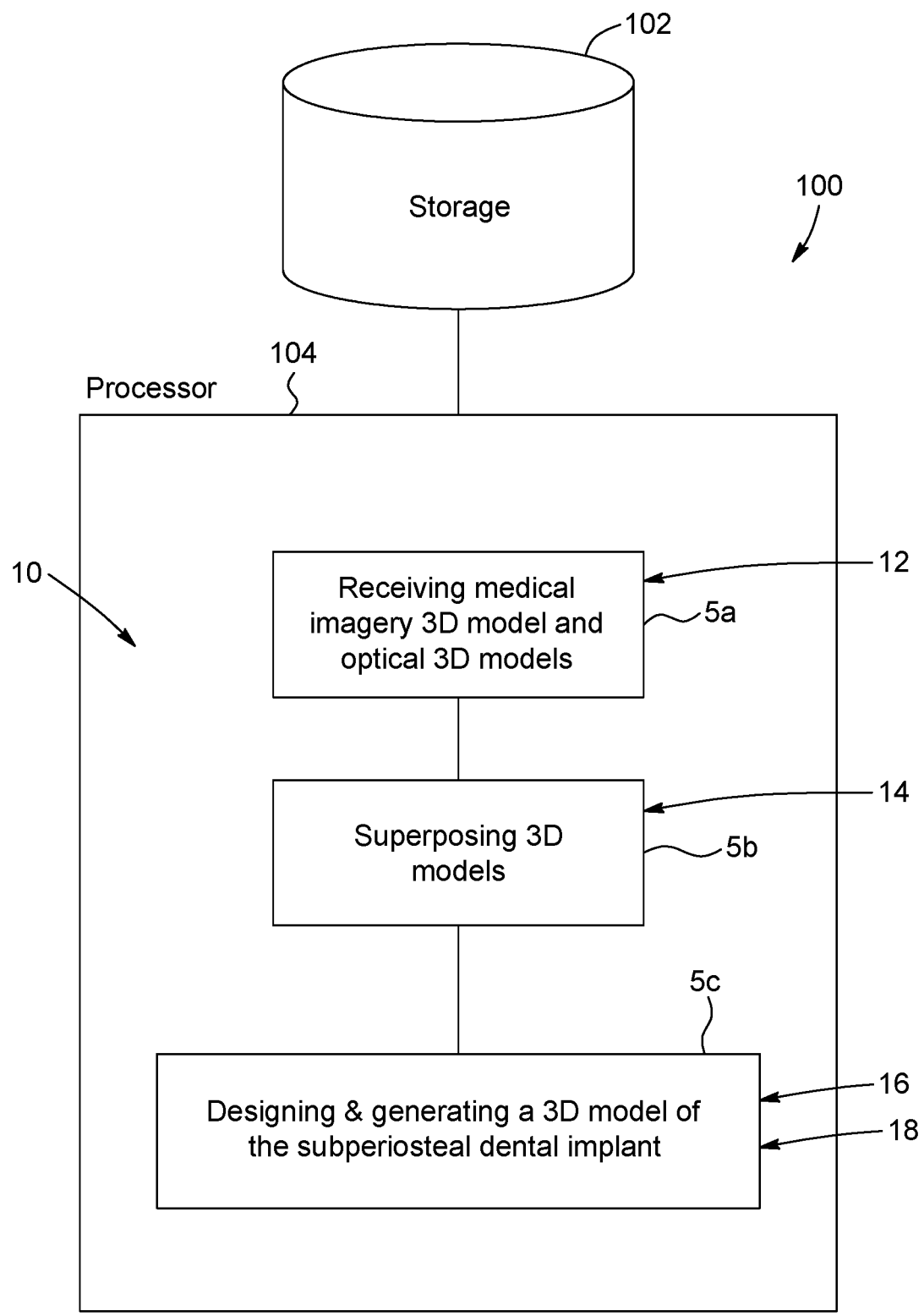
FIG. 1B is a bloc diagram of a system for generating a model of a subperiosteal dental implant device, according to an embodiment, the diagram further showing steps of a method executed by the system.

With reference to FIG. 1B and with further reference to FIGS. 2 to 12, one embodiment of a computer implemented method for performing the above described method for designing and generating a model of a subperiosteal dental implant device 10 will be described in more details below. The computer implemented method is executed by a computer system 100 comprising a storage medium 102 and a processor 104.

In the embodiment shown in FIG. 1B, the initial step of obtaining the mouth model of a patient (i.e. step 12 of the above described general method 10) includes storing, on the storage medium 102, acquired medical imagery images 130, such as CT scan images, (shown in FIGS. 6 and 7) of a diagnostic wax-up 118 including tooth models mounted on a jaw of the patient, an acquired optical 3D model 132 (shown in FIGS. 8 and 9) of the jaw of the patient and an acquired optical 3D model 134 (shown in FIGS. 10 and 11) of the tooth models 122 of the diagnostic wax-up 118. In an embodiment, the tooth models 122 of the diagnostic wax-up 118 are radiopaque tooth models. The initial step of obtaining a mouth model of a patient (i.e. step 12 of the above described general method 10) further comprises receiving, by the processor 104, the above-mentioned medical imagery images 130 and optical 3D models 132, 134. This step is represented by reference number 5a in FIG. 1B.

As mentioned above, in the course of the present description the term "medical imagery images" is used to refer to images acquired using a medical imaging method, such as, without being limitative, x-ray computed tomography images, MRI Images or the like, including bone information.

One skilled in the art will understand that, in alternative embodiments (not shown), only a subset of the medical imagery images 130 of a diagnostic wax-up 118 mounted on a jaw of the patient, the optical 3D model 132 of the jaw of the patient and the optical 3D model 134 of the tooth models 122 of the diagnostic wax-up 118 can be acquired and stored on the storage medium 102. Moreover, in an embodiment, the medical imagery images can show only the jaw of the patient (without a diagnostic wax-up mounted thereon), the existing teeth 142 extending from the jaw of the patient (if the patient has at least one existing tooth) and at least one toothless space for positioning at least one replacement tooth.

In the course of the present document, a "diagnostic wax-up" is understood to be a physical model of the at least one tooth model that is intended to be implanted in the mouth of the patient through engagement with the subperiosteal dental implant device. In an embodiment, in the "diagnostic wax-up", the at least one tooth model (which will be associated to the at least one replacement tooth) are mounted on a base which is shaped and sized to mate with a section of a gum line of the mouth of the patient, so that the diagnostic wax-up can temporarily be fitted in the mouth of the patient while the acquisition of the 3d model of the mouth of the patient including the diagnostic wax-up is performed. The diagnostic wax-up can also be temporarily fitted onto a model of the jaw of the patient.

Hence it will be understood that the medical imagery images 130 of the diagnostic wax-up 118 mounted on a jaw of the patient shows tooth models 122 of the diagnostic wax-up 118 and a jaw bone 140 of the jaw of the patient. In an embodiment where the patient has existing tooth or teeth, the medical imagery images 130 further show the existing teeth 142 extending from the jaw of the patient. In an embodiment, a 3D model 131 of the diagnostic wax-up 118 mounted on a jaw of the patient can be generated, by the processor 104, based on the medical imagery images 130.

In the course of the present description, the existing tooth or teeth can be natural tooth or teeth or a replacement tooth or teeth already secured to the patient's jaw.

Since the optical 3D model does not show internal geometry of the scanned elements (in opposition to the medical imaging), the optical 3D model 132 of the jaw of the patient shows a gum line 124 of the patient, and the existing teeth 142 of the patient extending therefrom (in the event where the patient has existing tooth or teeth). In the course of the present document, the optical 3D model 132 of the jaw is intended to include a 3D model obtained by scanning directly the patient's jaw or by scanning a physical model of the patient's jaw.

In the embodiment shown in FIG. 1B, the additional steps of positioning one or more replacement tooth in relation to the mouth model of the patient (i.e. step 14 of the above described general method 10) includes superposing, by means of the processor 104, the 3D model 131 obtained from the medical imagery images 130, the optical 3D model 132 of the jaw of the patient and the optical 3D model 134 of the tooth models 122 of the diagnostic wax-up 118. The superposition of the 3D models 131, 132, 134 defines a space 144 between the gum line 124 of the patient aligned with the tooth models 122 of the diagnostic wax-up 118 and the jaw bone 140. The space 144 corresponds to a gum tissue of the jaw of the patient. This step is represented by reference number 5b in FIG. 1B. The superposition of the 3D models 131, 132, 134 includes a shape of an external surface of the patient's jaw bone.

Using the data from the superposition of the 3D models 131, 132, 134 representing the at least one tooth model, the processor can extract the position of the at least one tooth model in relation to the jaw bone of the patient. One skilled in the art will understand that, in an alternative embodiment, the extraction of the position of the at least one tooth model in relation to the jaw bone of the patient can be performed using only a subset of the 3D models 131, 132, 134 representing the at least one tooth model. For example, in an embodiment where the 3D model 131 obtained from the medical imagery images 130 of the diagnostic wax-up 118 mounted on a jaw of the patient is of sufficient quality (of sufficient resolution), only the 3D model 131 obtained from the medical imagery images 130 could be used, i.e. the optical 3D model 134 of the tooth models 122 of the diagnostic wax-up 118 could be omitted.

It will be understood that, in an alternative embodiment where only a subset of the 3D models 130, 132, 134 are previously acquired and stored onto the storage medium, only the available 3D models are superposed during the step of superposing the 3D models.

Following steps 5a and 5b, in the embodiment shown in FIG. 1B, the additional steps of positioning one or more implant head at a respective implant position wherein each implant head is in alignment with a respective one of the one or more replacement tooth (i.e. step 16 of the above described general method 10) and designing and generating a model of the subperiosteal dental implant including the one or more implant head (i.e. step 18 of the above described general method 10) can be performed by the processor 104, using the data from the combined 3D model obtained from the superposition of the 3D model generated using the medical imagery images 130, optical 3D model 132 of the jaw of the patient, and the optical 3D model 134 of the tooth models 122 of the diagnostic wax-up 118. This step is represented by reference number 5c in FIG. 1B. The step of designing and generating the model of the subperiosteal dental implant can further include deriving a shape of a frame of the subperiosteal dental implant from an external shape of the jaw bone defined in the 3D model. In an embodiment, the derivation of the shape of the frame can include at least partially conforming the shape of the frame to the external shape of the jaw bone defined in the 3D model and, more particularly, a bone-facing surface of the frame.

In view of the above, the system 100 for designing and generating a model of a subperiosteal dental implant device shown in FIG. 1B, with further reference to FIGS. 3 to 12, comprises the storage medium 102 for storing the medical imagery images 130 of the diagnostic wax-up 118 mounted on the jaw 112, 114 of the patient. As mentioned above, in the embodiment shown, the medical imagery images 130 represents at least one tooth model 122 of the diagnostic wax-up 118 and a jaw bone 140 of the patient. In an embodiment, the medical imagery images 130 can also define a toothless space for positioning the at least one replacement tooth The storage medium 102 can also store a 3D model 132 of the jaw, representing a gum line 124 of a gum tissue, and a 3D model 134 of the tooth models 122 of the diagnostic wax-up 118.

The system 100 further comprises a processor 104 communicating with the storage medium 102 for generating the 3D model 131 from the medical imagery images 130 and for superposing the 3D models 131, 132, 134, to reveal a space between the gum line 124 and the jaw bone 140, at a location of the tooth models 122 of the diagnostic wax-up. As will be described in more details below, the space between the gum line 124 and the jaw bone 140 at the location of the tooth models 122 of the diagnostic wax-up corresponds to the gum tissue of the jaw. The processor 104 is further operative to design and generate a 3D model of the subperiosteal dental implant device based on the data of the superposed 3D models 131, 132, 134.

Now referring to FIG. 2, with further reference to FIGS. 3 to 12, a global process which allows the above described computer implemented method to be performed will be described in more details below.

In an embodiment, the initial step (step 1) of the global process is performed at a dentist's facility. This initial step (step 1) includes the steps of taking an impression of a patient's maxillary and mandibular jaws using a dental impression material. The impression of the maxillary and mandibular jaws of the patient provide the molds which will subsequently be used to make a physical model of the maxillary and mandibular jaws of the patient, as will be described in more details below. In an embodiment, an impression of only one of the patient's maxillary and mandibular jaws can be taken. In an embodiment, this initial step (step 1), also includes the taking of an impression of the articulation between the maxillary and mandibular jaws and sending the impressions of the maxillary and mandibular jaws and articulation therebetween to a laboratory for the subsequent steps to be performed. One skilled in the art will understand that any type of known dental impression material can be used to take the above mentioned impressions.

In an embodiment, the second step (step 2) of the global process is performed at the laboratory. The second step (step 2) includes making an intermediary physical model 112, 114 of the maxillary and the mandibular jaws of the patient, from the impressions of the maxillary and mandibular jaws and assembling the intermediary physical models 112, 114 in accordance with the articulation of the patient defined by the previously taken impression of the articulation between the maxillary and mandibular jaws of the patient. The assembled intermediary models 112, 114 of the maxillary and the mandibular jaws of the patient yields a final physical model 116 of the patient's jaws (see FIG. 3). In an embodiment, the intermediary models 112, 114 of the maxillary and the mandibular jaws of the patient can be made using dental gypsum, but one skilled in the art will understand that, in alternative embodiments any suitable modeling material can also be used.

In an alternative embodiment, these first steps can be replaced by obtaining an intraoral optical scan of at least a section of the patient's mouth. The intraoral optical scan will include information about the patient's gum line, the existing tooth/teeth (if any) and/or toothless spaces of the jaw of the patient.

The second step (step 2) also includes building a diagnostic wax-up 118 representing tooth implants (i.e. tooth models). Each one of the tooth models of the diagnostic wax-up will be associated to a replacement tooth to be implanted into the jaw(s) of the patient. As mentioned above and can be seen in FIG. 4, the diagnostic wax-up 118 comprises a base 120, onto which at least one tooth model 122 is mounted. The base 120 is adapted to fit onto a corresponding one of the jaws 114 of the final model 116 (i.e. the maxillary jaw and/or the mandibular jaw of the final model 116) or onto the gum tissue of the patient's jaw. More particularly, the base 120 defines an undersurface 146 which is shaped to mate with a portion of the corresponding one of the jaws 114 representing the gum line of the mouth of the patient (see FIGS. 3 to 5). In an embodiment, the at least one tooth model 122 is selected from a catalog of tooth models and represent the at least one model/replacement tooth and its position in the mouth of the patient. This second step (step 2) finally includes sending the final model 116 and the diagnostic wax-up 118 to the dentist facility for the subsequent steps to be performed.

In an embodiment, the third step (step 3) of the global process is once again performed at the dentist's facility. This third step (step 3) includes fitting the diagnostic wax-up 118 in the mouth of the patient, over the respective one of the jaw(s) of the patient and performing a medical imaging of the mouth of the patient, with the wax-up 118 fitted therein. The medical imaging of the mouth of the patient, such as and without being limitative a CT scan, with the wax-up 118 fitted therein, produces the above-mentioned medical imagery images 130 of the jaw(s) of the patient (schematically represented in FIG. 6). In an embodiment, the medical imagery images 130 define (or show) both the maxillary and mandibular jaws of the patient. However, it is appreciated that, in alternative embodiments, the medical imagery images can show only the respective one of the maxillary and mandibular jaws. As mentioned above, in the embodiment shown, the medical imagery images 130 represent the tooth models 122 of the diagnostic wax-up 118 (which can be radiopaque to be included in the medical imagery images 130 with some imaging technologies), a jaw bone 140 of the jaw(s) and the existing teeth 142 of the jaw (if any).

Figure 6:
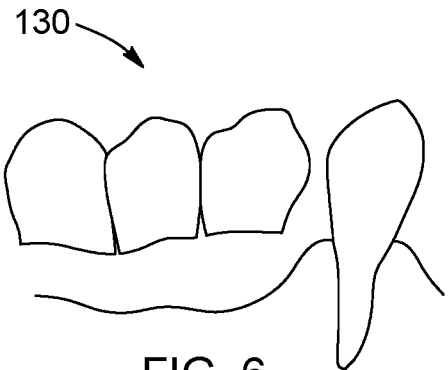
FIG. 6 is a schematic representation of a section of a medical imagery image showing existing and replacement teeth above a bone line and being produced by a step of a method performed by the system shown in FIG. 1B.
Figure 7:
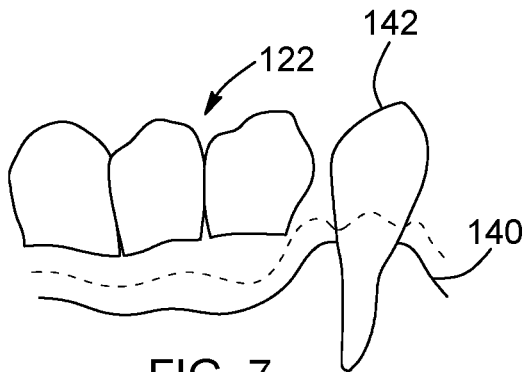
FIG. 7 shows the schematic representation of FIG. 6 when superposed with other images including a gum line, the other images being shown in broken lines.

As can be better seen in FIGS. 6 and 7, in the medical imagery images 130, the tooth models 122 are spaced-apart from the jaw bone 140 (i.e. the tooth models 122 are shown "floating" over the jaw bone 140). FIG. 7 schematically shows the components represented in the medical imagery images 130 of FIG. 6, namely, the tooth models 122, the tooth 142 and the jaw bone 140, in relation to other components (including a gum line) represented with a broken line. In an embodiment, the third step (step 3) also includes storing the medical imagery images 130 on a storage medium, such as, without being limitative, a USB key, a compact disk (CD), or the like and sending the storage medium to an imaging facility.

One skilled in the art will readily understand that, in an alternative embodiment, the medical imagery images 130 can also be stored on a memory of a computer and can be securely transmitted over a data communication network, such as, for example and without being limitative, a local area network (LAN) or a wide area network (WAN), such as the Internet, or any other suitable data communication means, as will be readily understood by a skilled reader.

In an embodiment, the fourth step (step 4) of the global process is performed at the imaging facility. This fourth step (step 4) includes receiving the medical imagery images 130, the final model 116 and the diagnostic wax-up 118 at the imaging facility. The fourth step (step 4) can also include the step of converting the medical imagery images 130 into a 3D model 131 of the jaw(s) of the patient, for instance if the medical imagery images are CT scan images. In other words, during this fourth step (step 4), a 3D model 131 of the jaw of the patient is generated using the transmitted medical imagery images 130. One skilled in the art will understand that, in an alternative embodiment, the 3D model 131 of the jaw of the patient can be previously generated and transmitted to the imaging facility. Methods for converting medical imagery images into 3D models are well-known and need not be described in details herein.

Figure 8:
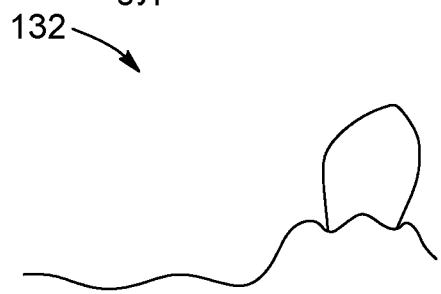
FIG. 8 is a schematic representation of a section of a second image showing existing teeth protruding from the gum line and being produced by a step of a method performed by the system shown in FIG. 1B.
Figure 9:
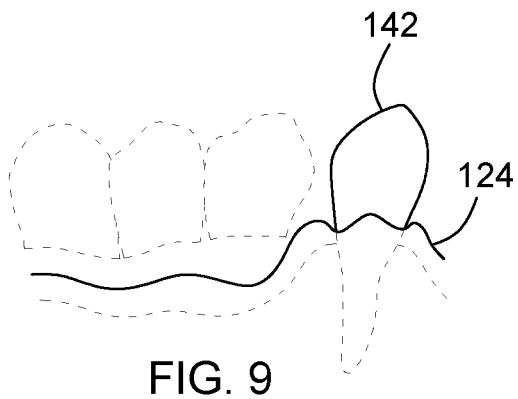
FIG. 9 shows the schematic representation of FIG. 8 when superposed with other images including the replacement teeth and the bone line, the other images being shown in broken lines.

In an embodiment, the fourth step (step 4) also includes performing a three-dimensional optical scan of the physical intermediary model 112, 114 of the maxillary and the mandibular jaws in order to obtain the above-mentioned optical scan 3D model 132 of the jaw of the patient, schematically illustrated as a 2D image at FIG. 8. The optical scan 3D model 132 of the model of the jaw of the patient provides a data model of the patient's existing teeth 142 and gum line 124, which are schematically shown in FIG. 9 in relation to other components represented in broken lines. Alternatively, the optical scan to obtain the 3D model 132 of the jaw of the patient can also be performed intraorally, i.e. directly in the patient's mouth, to provide a data model of the patient's existing teeth 142 and gum line 124.

Figure 10:
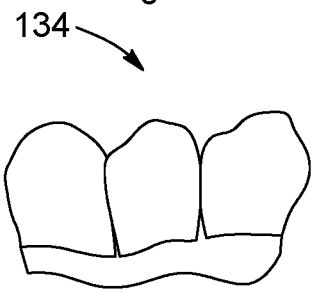
FIG. 10 is a schematic representation of a section of a third image showing the replacement teeth and the gum line and being produced by a step of a method performed by the system shown in FIG. 1B.
Figure 11:
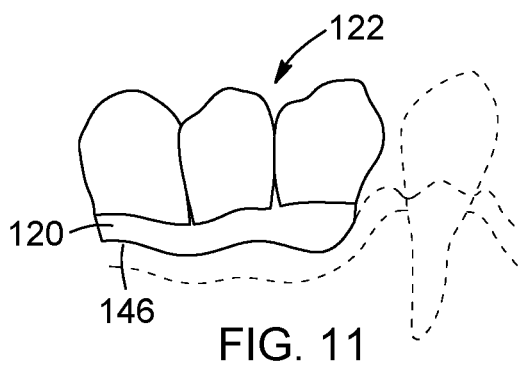
FIG. 11 shows the schematic representation of FIG. 10 when superposed with other images including existing teeth and the bone line, the other images being shown in broken lines.

In an embodiment, the fourth step (step 4) further includes performing a three-dimensional optical scan of the diagnostic wax-up 118 in order to obtain the above-mentioned optical scan 3D model 134 of the tooth models 122 of the diagnostic wax-up 118, schematically illustrated as a 2D image at FIG. 10. The optical scan 3D model 134 of the tooth models 122 of the diagnostic wax-up 118 provides a three-dimensional model of the entire diagnostic wax-up 118 (including the base 120 and the tooth models 122), as schematically represented as a 2D image in FIG. 11. The optical scan 3D model 134 thus provides a data model of the shape and contour of the tooth models 122 and of its base 120, including the undersurface 146 which conforms to the shape of the gum line 124. The optical scan 3D model 134 of the tooth models 122 of the diagnostic wax-up 118 provides more precise contour information of the tooth models in comparison to the medical imagery 3D model 131 which can include some imperfections in the representation of the tooth models 122.

One skilled in the art will understand that, in an alternative embodiment, the diagnostic wax-up 118 can be subjected to the three-dimensional optical scan when engaged with the respective one of the intermediary model 112, 114 of the maxillary and the mandibular jaws. Alternatively, the diagnostic wax-up 118 can be subjected to the three-dimensional optical scan when engaged with the jaw of the patient.

In an embodiment, the fifth step (step 5) of the global process is also performed at the imaging facility. This fifth step (step 5) encompasses steps 5a, 5b and 5c of the method described above and shown in FIG. 1B.

Hence, in an embodiment, the fifth step (step 5), includes superposing, via the processor 104, the 3D model 131 of the jaw(s) of the patient obtained from the medical imagery images, the 3D model 132 of the jaw of the patient obtained from the optical scan, and the 3D model 134 of the tooth models 122 of the diagnostic wax-up 118.

Figure 12:
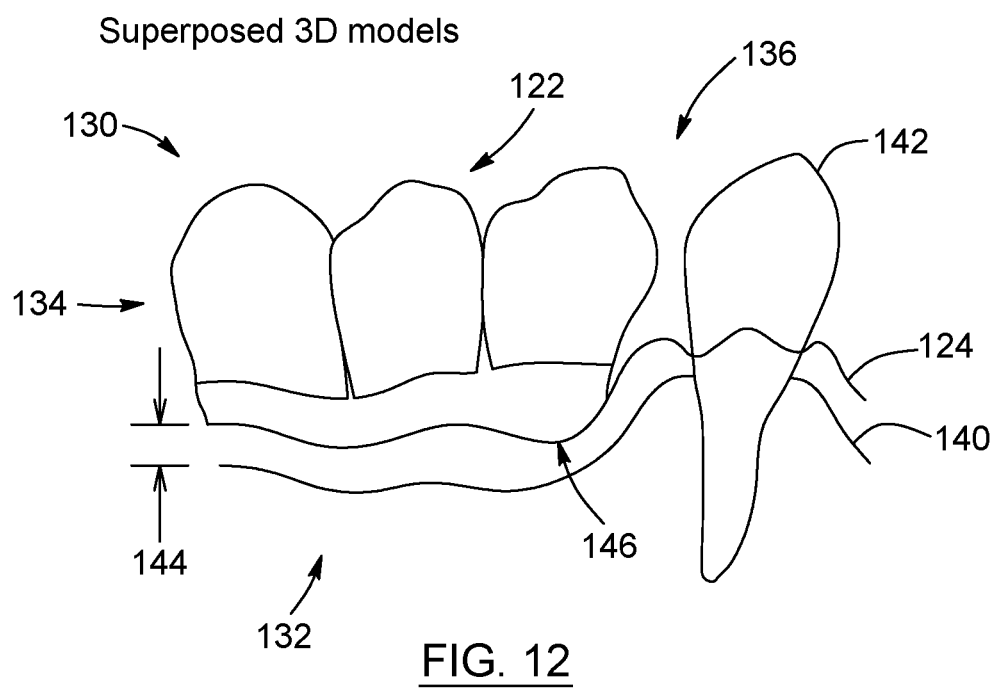
FIG. 12 is a schematic representation of the images of FIGS. 6, 8 and 10 superposed together.

The model obtained through the superposition is a combined 3D model 136 schematically represented as a 2D image in FIG. 12. The combined 3D model 136 includes the features of each one of the models 131, 132, 134. Thus, the combined 3D model 136 resulting from the step of superposing the 3D models 131, 132, 134 comprises data regarding the shape of the jaw bone 140 of the patient, extracted from the medical imagery images 130 and converted into the 3D model 131 of the mouth of the patient. The combined 3D model 136 also includes data regarding the outer shape of the gum tissue 124, extracted from the optical scan 3D model 132 of the model jaws 112, 114. The combined 3D model 136 further includes data regarding the shape and position of each of the tooth models 142, obtained from the medical imagery images 130 converted into the 3D model 131 of the mouth of the patient including the diagnostic wax up 118 and/or the optical scan 3D model 134 of the diagnostic wax up 118. Finally, the combined 3D model 136 includes data regarding the thickness of the gum tissue 144, based on a space between the gum line 124 and the jaw bone 140 and extracted from the superposition of the optical scan 3D model 132 and the medical imagery 3D model 131.

In an embodiment, the step of superposing the 3D models 131, 132, 134 includes aligning the existing teeth 142 of the patient in the medical imagery 3D model 131 and the optical scan 3D model 132. In an embodiment, this step further includes aligning the undersurface 146 of the tooth models 122 of the optical scan 3D model 134 of the tooth models 122 of the diagnostic wax-up 118 with a corresponding portion of the gum line 124 of the optical scan 3D model 132 of the jaw of the patient obtained from the optical scan.

In the alternative embodiment where the diagnostic wax-up 118 is subjected to an optical scan when engaged with the respective one of the model jaws 112, 114, the step of superposing the 3D models 131, 132, 134 can include aligning the patient's existing teeth 142 of all 3D models 131, 132, 134.

One skilled in the art will easily understand that, in alternative embodiments, numerous different alignment means and/or methods can also be used in order to superpose the 3D models 131, 132, 134. For example, and without being limitative, in the absence of any teeth in the mouth of the patient, the 3D model 131 can be aligned with the optical scan 3D model 134 (instead of with the optical scan 3D model 132) based on the positioning of the tooth models 122.

Thus, in an embodiment where the section of the patient's mouth includes at least one existing tooth 142, medical imaging can be performed without the diagnostic wax-up 118. In such an embodiment, a 3D model 131 of the section of the patient's mouth including information about the jaw bone 140 and the at least one existing tooth 142 (including toothless spaces therebetween) is obtained. The optical scan 3D model 132 can be obtained subsequently, either intraorally or from a physical model of the patient's jaw(s). The optical scan 3D model 132 includes information about the gum line 124 of the gum tissue of the patient and the at least one existing tooth 142 (including toothless spaces). The optical scan 3D model 134 of the diagnostic wax up 118, including the tooth models 122, can be obtained by several methods. The diagnostic wax up 118 can be optically scan alone, mounted on the patient's jaw (intraoral scan), or mounted on the physical model of the patient's jaw(s). If the diagnostic wax up is scanned alone, the optical scan 3D model 134 includes information about the gum line 124 and the tooth models 122. On the contrary, if the diagnostic wax up is scanned mounted on the patient's jaw or on the physical model, the optical scan 3D model 134 includes information about the tooth models 122 and the at least one existing tooth 142. If the diagnostic wax up 118 is optically scanned alone, it is aligned with the optical scan 3D model 132 using the gum line 124 while the models 131, 132 are aligned using the at least one existing tooth 142. If the diagnostic wax up 118 is optically mounted on the patient's jaw or on the physical model, the three models 131, 132, and 134 can be aligned using at least one existing tooth.

In an alternative embodiment, instead of taking an optical scan 3D model 134 of the diagnostic wax up, the replacement tooth/teeth can be positioned with respect to the superposed 3D models 131, 132 using information contained in a virtual library including model/replacement tooth/teeth. More particularly, the model/replacement tooth/teeth can be picked from a virtual library of objects, wherein each object represents a replacement tooth having a desired shape to fill a toothless space in the dentition of the patient and the positioning of each digital tooth in relation to the superposed 3D models 131, 132 of the patient can be performed using a computer-aided design (CAD) technology.

Once again, in an embodiment where the section of the patient's mouth includes at least one existing tooth 142, the medical imaging can be performed with the diagnostic wax-up 118 being mounted on the patient's jaw. Thus, a 3D model 131 of the section of the patient's mouth including the jaw bone, the at least one existing tooth 142, and the tooth models 122 is obtained. The optical scan 3D model 132 can be obtained as detailed above, either intraorally or from a physical model of the jaw(s) and includes information about the gum line 124 and the at least one existing tooth 142. Optionally, an optical scan 3D model 134 of the diagnostic wax up 118 can be obtained. As detailed above, the diagnostic wax up 118 can be optically scan alone, mounted on the patient's jaw (intraoral scan), or mounted on the physical model of the patient's jaw(s). The models 131, 132 are aligned using the at least one existing tooth 142. The optical scan 3D model 134 is aligned with the 3D model 131 with the tooth models 122, or with the optical scan 3D model 132 using the gum line 124 if it is scanned alone, or with the models 131 and/or 132 using the at least one existing tooth 142, if scanned mounted on the patient's jaw or the physical model.

As mentioned above, in an embodiment, the method can be carried without the optical scan 3D model 134 of the diagnostic wax up 118. In such an embodiment, the information about the tooth models 122 is obtained solely from the medical imaging performed with the diagnostic wax-up 118 being mounted on the patient's jaw.

Still alternatively, in an embodiment where the section of the patient's mouth is free of existing tooth, the medical imaging can also be performed with the diagnostic wax-up 118 being mounted on the patient's jaw. Thus, a 3D model 131 of the section of the patient's mouth including the bone and the tooth models 122 is obtained. The optical scan 3D model 132 can be obtained as detailed above, either intraorally or from a physical model of the jaw(s) and includes information about the gum line 124. An optical scan 3D model 134 of the diagnostic wax up 118 can also be obtained. To obtain the optical scan 3D model 134 of the diagnostic wax up 118, the diagnostic wax up 118 is optically scanned alone and includes information about the gum line 124 and the tooth models 122. The models 132, 134 can be aligned using the gum line 124 while the models 131, 134 can be aligned using the tooth models 122.

In an embodiment, the fifth step (step 5), further includes the step of designing and generating a 3D model of the subperiosteal dental implant device and storing the generated 3D model on the storage medium 102. In an embodiment, the generated 3D model of the subperiosteal dental implant device can also be sent (or transmitted) to a fabrication facility. For example and without being limitative, the generated 3D model of the subperiosteal dental implant device can be transmitted to the fabrication facility over a data communication network (as described above) or other suitable transmission means or methods.

In an embodiment, the 3D model of the subperiosteal dental implant device can be generated using a modeling tool such as a computer-aided design (CAD) tool. As will be described in more details below, the 3D model of the subperiosteal dental implant device defines a framework to fit onto the jaw bone 140 of the patient, as well as the replacement teeth and any other component of the implant system (such as implant heads, etc.). Moreover, as will also be described in more details below, the 3D model of the subperiosteal dental implant device can include a component corresponding to an implant head 150 (see FIGS. 13 and 14a to 14c) for one or more of the replacement teeth.

In an embodiment, during the fifth step (step 5), the generated 3D model can be approved or validated by a dentist. For example and without being limitative, in an embodiment, the generated 3D model of the subperiosteal dental implant device can be sent to the dentist over a data communication network (as described above) or other suitable transmission means or methods, for validation thereof. Upon validation of the generated 3D model by the dentist, the generated 3D model of the subperiosteal dental implant device can be sent to a fabrication facility. Once again, the generated 3D model of the subperiosteal dental implant device can be sent to the fabrication facility over a data communication network (as described above) or other suitable transmission means or methods.

In an embodiment, the sixth step (step 6) of the global process is performed at a fabrication facility. This sixth step (step 6) includes receiving the 3D model of the subperiosteal dental implant device and fabricating a frame 162 of the subperiosteal dental implant device 160 (see FIG. 17), as described in more details below, in accordance with the received 3D model of the subperiosteal dental implant device. In an embodiment, the frame 162 of the subperiosteal dental implant device is built with at least a portion of the implant heads 150, as will once again be described in more details below.

When designing the frame 162 of the subperiosteal dental implant device, an external shape of the jaw bone can be taken into account. The thickness of the gum tissue can also be considered. For instance, the shape of the frame 162 can be at least partially derived from the external shape of the jaw bone. More particularly, the shape of the frame 162 can be designed to at least partially conform to the external shape of the jaw bone. In an embodiment, a bone-facing surface of the frame 162 substantially conforms to the external shape of the jaw bone and, thus, the frame 162 can be superposed to the jaw bone in a single position. As mentioned above, the external shape of the jaw bone is obtained from the medical imaging. In an embodiment, the thickness of the frame 162 can be designed to be thinner than the gum tissue with only implant heads 150 protruding from the gum tissue. As mentioned above, the implant heads 150 are substantially aligned with the replacement tooth/teeth of the 3D model including at least the jaw bone, the gum line, and the replacement tooth/teeth, such as the combined 3D model 136. The implant heads 150 are positioned on the frame 162 of the subperiosteal dental implant device 160 in alignment with a respective one of the one or more replacement tooth/teeth. A height of the implant heads 150 can be selected/designed based on a thickness of the jaw gum. In an embodiment, the implant heads 150 extend close to an external surface of the gum tissue (i.e. the gum line) or slightly protrude above the gum tissue when the subperiosteal dental implant device is sited on the jaw bone and covered with the gum tissue. The implant heads 150 end in the vicinity of the gum line, either slightly below, slightly above, or aligned therewith. Moreover, it will be understood that the implant heads 150 can be angled to adapt to the external shape of the jaw bone and the corresponding shape of the frame 162 at least partially derived from the external shape of the jaw bone 140, at the respective specific section where the implant heads 150 are positioned.

In an embodiment, the implant heads 150 are first positioned with respect to the model of the jaw bone. As mentioned above, the implant heads 150 are positioned to be substantially aligned with a respective one of the tooth model 122 (i.e. with a respective one of the replacement tooth/teeth of the 3D jaw model). Then, the frame 162 is designed. The frame 162 can be a mesh with interconnected segments intersecting with the implant heads, i.e. the position of the implant heads. As mentioned above, the shape of the frame 162 is designed to at least partially conform to the external shape of the jaw bone, with a thickness thinner that the corresponding section of the gum tissue.

The frame 162 of the subperiosteal dental implant device, including at least a portion of the implant heads 150, can be manufactured with any suitable CAM technique such as and without being limitative, machining and 3D printing including laser sintering.

One skilled in the art will understand that numerous modifications could be made to the above-described method, overall process, or system without departing from the scope of the present invention.

For example, one skilled in the art will understand that the non-invasive methods which can be used in order to obtain the mouth model of the patient are not limited to the above described methods and any non-invasive method which is known to provide the necessary data for obtaining the mouth model of the patient can be used. It will be understood that the term "non-invasive method" is used herein to refer to a method which does not involve the cutting of tissue in order to expose the jaw bone for the purpose of obtaining the profile of the jaw bone. In other words, in a "non-invasive method", the profile of the dentition and jaw bone of the patient is obtained without surgery or the like.

For example and without being limitative, in an embodiment, the mouth model of the patient can be obtained through a combination of an intra-oral scanning of the mouth of the patient and a medical imaging thereof. In such an embodiment, the intra-oral scanning of the mouth of the patient is performed to obtain three-dimensional surface information of the existing teeth and jawline (or gum line 124) of the patient. The medical imaging is performed to obtain information regarding the contour of the jaw bone as well as of the existing teeth of the patient (if any). In such an embodiment, the mouth model of the patient can be obtained by matching the region in both imaging data corresponding to the existing teeth. One skilled in the art will easily understand that, in such an embodiment, the medical imagery images are required to have a resolution sufficient to generate a 3D model therefrom that has a resolution sufficient to allow subsequent superposition with 3D models obtained from the intra-oral scanning of the mouth of the patient with sufficient precision.

In an alternative embodiment, the optical 3D model 132 can be taken directly from the mouth of the patient using appropriate scanning devices and technologies, without resorting to a physical impression of the jaw of the patient.

In another alternative embodiment, the shape of the jaw bone of the patient for the 3D model can be obtained by providing a 3D model obtained via intra-oral scanning, and by approximating the surface of the jaw bone, based on an assumption that the gum tissue covering the jaw bone is substantially even and of a known thickness, such as, for example and without being limitative, about 1 mm.

Similarly, in accordance with an embodiment, the positioning of the replacement tooth/teeth in relation to the mouth model of the patient can include the steps of obtaining the profile of the jaw bone (e.g. via the medical imagery images); determining the surface of the gum tissue covering the jaw bone either based on an assumption that the gum tissue covering the jaw bone is substantially even and of a known thickness (for example about 1 mm) or via the model of the jaw of the patient obtained from the intra-oral scan of the jaw of the patient; defining at least one toothless space for inserting the at least one replacement tooth using the mouth model; and positioning the replacement tooth/teeth in relation to the mouth model, to extend beyond the gum line.

In an embodiment, the replacement tooth/teeth can be picked from a virtual library of objects stored on the above-mentioned storage medium 102, wherein each object represents a replacement tooth having a desired shape to fill a toothless space in the dentition of the patient and the positioning of each digital tooth in relation to the mouth model of the patient can be performed using a computer-aided design (CAD) technology.

Thus, information concerning one of the jaw bone and the gum line can be obtained from one of the medical imagery images and the optical scan images respectively. Information about the other one of the jaw bone and the gum line can be approximated using the scanned information. For instance, if information about the jaw bone is obtained from the medical imagery images, information about the gum line can be approximated by making the assumption that gum tissue covering the jaw bone is substantially even and of a known thickness and by adding the known thickness to the model of the jaw bone. On the contrary, if information about the gum line is obtained from the optical scan images, information about the jaw bone can be approximated by making the assumption that gum tissue covering the jaw bone is substantially even and of a known thickness and by subtracting the known thickness to the model of the gum line. The positioning of the replacement tooth/teeth can be obtained through scanning of a diagnostic wax up including tooth models (either alone, intraorally when mounted on a patient's jaw, or mounted on a physical model of the patient's jaw). Alternatively, the positioning of the replacement tooth/teeth can be performed with CAD technology using virtual models of the replacement tooth/teeth.

Moreover, it will easily be understood that the any of the above steps of the general process (see FIG. 2) or portions thereof can be made at a facility different from the one of the embodiment shown, such location being simply given as a general indicator of the typical procedure. For example, in an embodiment, the above steps of the general process can all be performed in one or only a subset of the dentist facility, laboratory, the imaging facility and the fabrication facility.

Subperiosteal Dental Implant Device and Corresponding Dental Implant System

Embodiments of a method 10 for generating a model of a subperiosteal dental implant device and fabricating the dental implant device having been described in details above, the generated subperiosteal dental implant device 160 will now be described in more details below.

Figure 13:
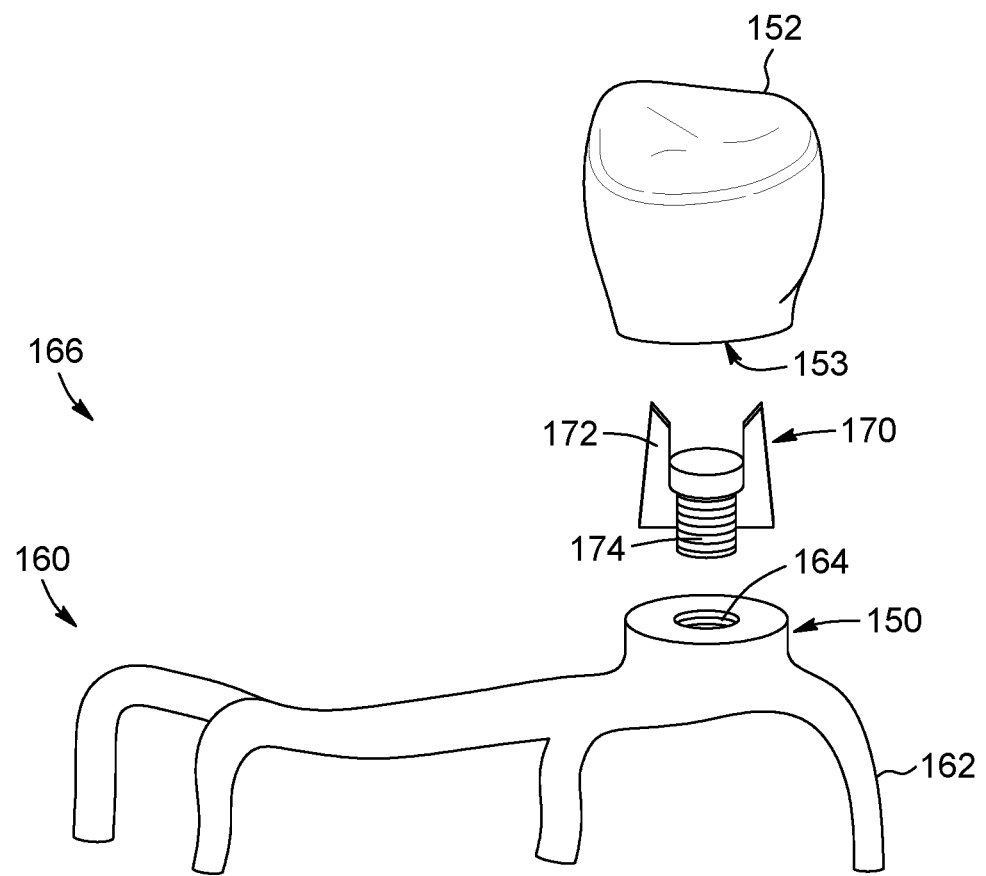
FIG. 13 is an exploded view of a dental system including a subperiosteal dental implant device.

Referring to FIG. 13, there is shown a dental implant system 166 including the subperiosteal dental implant device 160 and one or more connector 170 securable (or removably engageable with) to the subperiosteal dental implant device 160.

The subperiosteal dental implant device can be a partial subperiosteal dental implant device or a total subperiosteal dental implant device. The partial subperiosteal dental implant device is designed to engage only a section of one of the patient's jaw, i.e. the patient's mouth includes at least one existing tooth. Embodiments of a partial subperiosteal dental implant device are shown in FIGS. 13 and 14a to 14c. A total subperiosteal dental implant device is designed to engage an entire (or substantially entire) patient's jaw. An embodiment of a total subperiosteal dental implant device is shown in FIG. 15.

The subperiosteal dental implant device 160 comprises the frame 162 (also referred herein as "framework"). The frame 162 is designed to be mounted onto and, more particularly, sit on the external surface of the jaw bone of the patient, as mentioned above. The subperiosteal dental implant device 160 further comprises one or more implant heads 150 extending from the frame 162, or at least a portion thereof (only one is shown in FIG. 13 but it is appreciated that the subperiosteal dental implant device 160 can include more than one implant head 150). The implant head(s) 150, or at least a portion thereof, can be integral (or single piece) with the frame 162, i.e. they can be manufactured simultaneously with the frame 162 as a single piece. Each implant head 150 is configured to engage with one replacement tooth 152, which can be connected to one or more adjacent replacement teeth. In the particular embodiment shown in FIG. 13, the frame 162 has one implant head 150, configured to receive one replacement tooth 152. The implant head 150 has an internally threaded socket 164 adapted to receive a connector 170 to provide an engagement between the replacement tooth 152 and the implant head 150.

In the embodiment shown, the connector 170 is an abutment, but one skilled in the art will understand that any type of connector 170 can be used. The connector 170 comprises an externally threaded end section 174 for engaging with the threaded socket 164 of the implant head 150, and a connecting head 172 opposite the threaded end section 174 and protruding from the implant head 150 when engaged therewith, for connecting with the replacement tooth 152. The replacement tooth 152 comprises an opening 153 shaped to mate with the connecting head 172 of the connector 170. For example and without being limitative, the connecting head 172 can be cemented with the replacement tooth 152.

As described above, the one or more connector 170 is configured to receive one or more replacement tooth 152 and connect the one or more replacement tooth 152 with the subperiosteal dental implant device 160. The modular configuration of the above-described dental implant head system 166 facilitates the replacement of components, such as the replacement tooth/teeth, without requiring surgery and/or without having to replace or repair the frame 162 of the subperiosteal dental implant device 160.

One skilled in the art will understand that, in alternative embodiments, the shape of the connector 170 can vary from the embodiment shown in FIG. 13. Furthermore, in another alternative embodiment, the connector 170 can be permanently secured to the implant head 150, such as by cementation, rather than being detachably engaged thereto, such as, by complementary threaded connections as described above.

One skilled in the art will also understand that, in an alternative embodiment, the dental implant system 166 can be free of connector 170 and the replacement tooth or teeth 152 can be secured directly to the implant head 150. Once again, the replacement tooth or teeth 152 can be secured to the implant head 150 permanently.

The connector(s) can be selected from a connector library for which virtual models can exist. The connector can be selected based on a toothless space available between two adjacent teeth and a height of the gum tissue and/or the replacement tooth. Variable parameters for the connectors include, but are not limited to, their height, their diameter, an interior socket diameter, etc. Alternatively, the connector(s) can be custom-made.

Figure 14A:
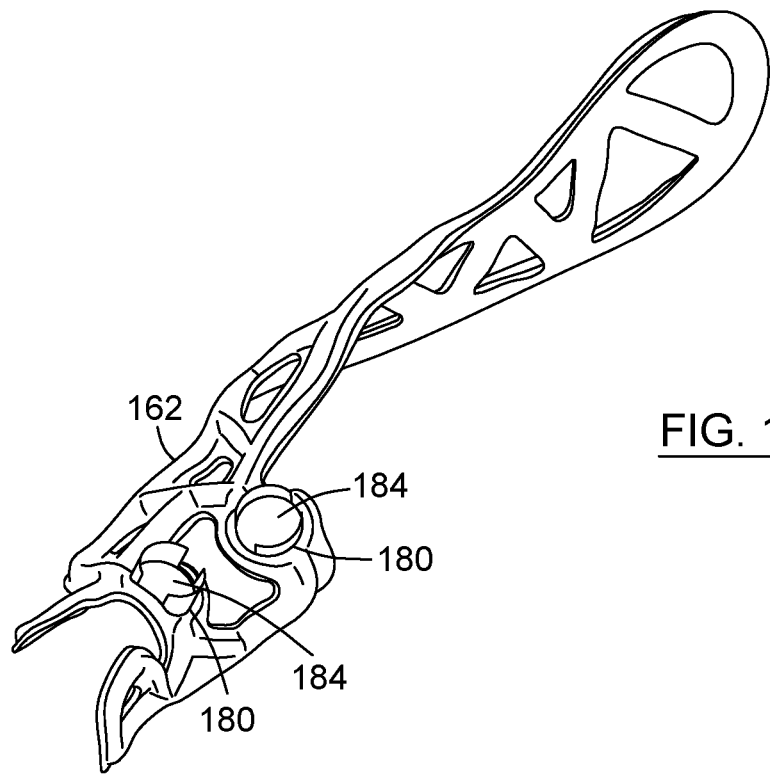
Figure 14B:
Figure 14C:
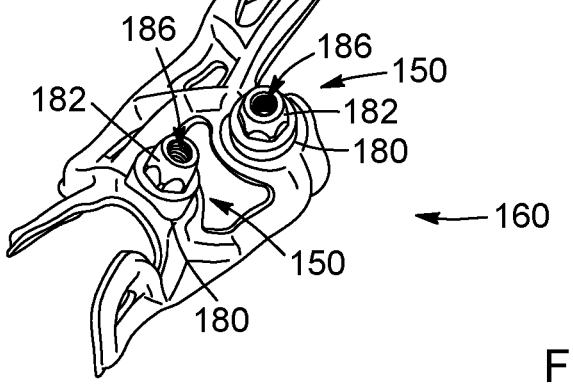
Figure 15:
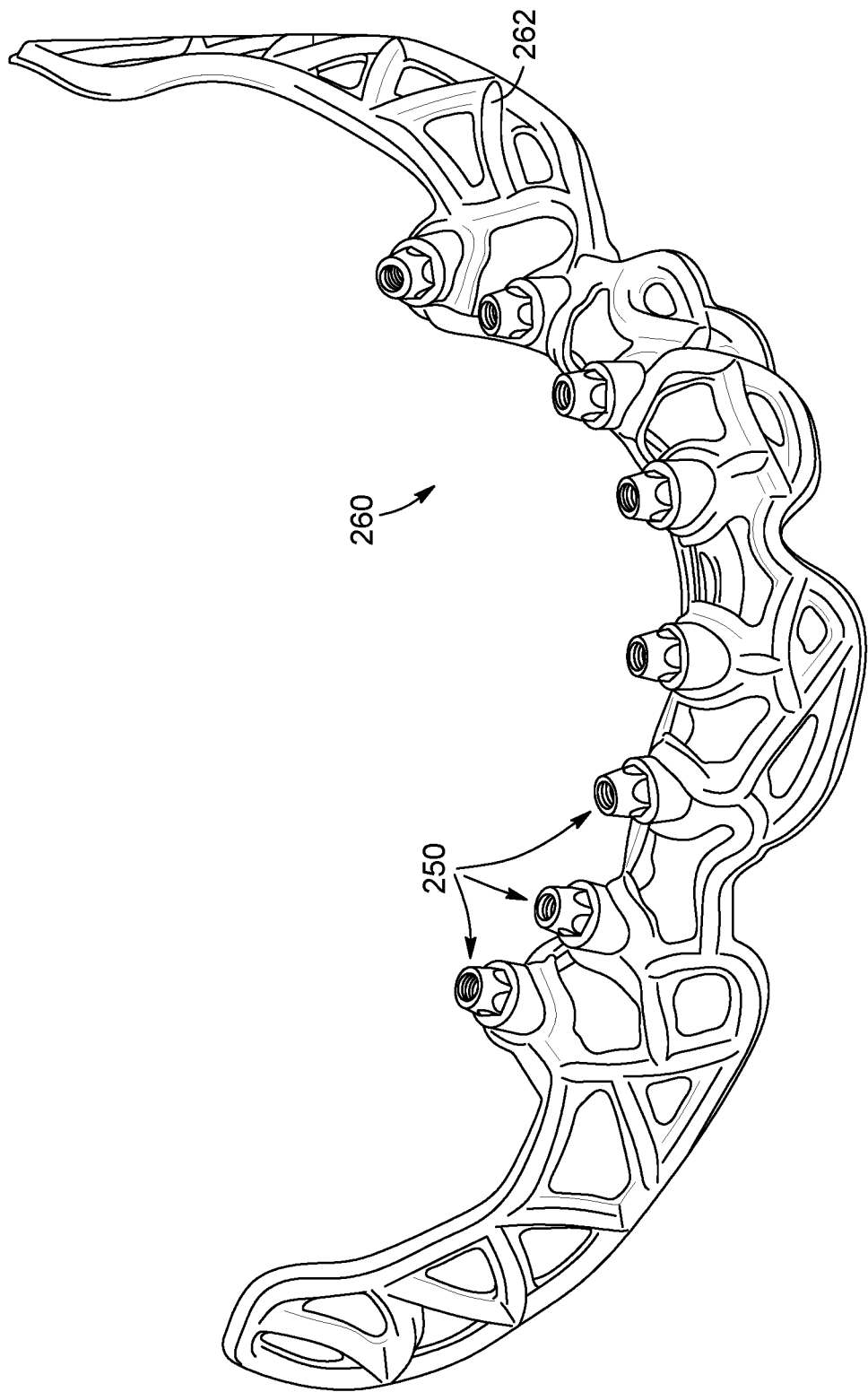
FIG. 15 is a perspective view of a total subperiosteal dental implant device in accordance with an embodiment and including eight implant heads integral with a frame of the total subperiosteal dental implant.

Referring now to FIGS. 14a to 14c, there is shown an alternative embodiment of a subperiosteal dental implant device 160, wherein the subperiosteal dental implant device 160 is a partial subperiosteal dental implant device 160. In the embodiment shown, two implant heads 150 (or portions thereof) extend from the frame 162. Each one of the implant heads 150 includes two components: a receiving portion 180 and a head portion 182. In an embodiment, the receiving portion 180 is integral with the frame 162 and is manufactured simultaneously therewith. In the embodiment shown, the receiving portion 180 has a substantially circular cavity 184 defined therein. One skilled in the art will however understand that the shape of the cavity 184 can vary from the embodiment shown in FIG. 14a. The cavity 184 is shaped to receive therein the head portion 182. The head portion 182 is manufactured independently from the frame 162 and the receiving portions 180 of the implant heads 150. The head portion 182 is engageable in the cavity 184 and securable to the receiving portion 180. In the embodiment shown, the head portion 182 is cemented to the receiving portion 180. Once again, one skilled in the art will understand that the shape of the head portion 182 and/or the receiving portion 180 can however vary from the embodiment shown in FIGS. 14b and 14c.

In the embodiment shown, the head portion 182 includes an internally threaded socket 186 designed to receive either a connector 170 or a replacement tooth 152. In an alternative embodiment, where, for example, the head portion 182 is designed to connect with the replacement tooth 152, the head portion 182 can also be free of internally threaded socket.

In an alternative embodiment, the implant head 150 can be single piece, i.e. without engageable receiving portion 180 and head portion 182. Thus, the frame 162 can be manufactured as a single piece with the implant head(s) 150 including a section corresponding to the head portion(s) 182.

Now referring to FIG. 15, there is shown an alternative embodiment of a subperiosteal dental implant device 260, wherein the subperiosteal dental implant device 260 is a total subperiosteal dental implant device 260 and wherein similar features are numbered using the same reference numerals in the 200 series. As mentioned above, in opposition to a partial subperiosteal dental implant device 160 as shown in FIGS. 14a and 14c, a total subperiosteal dental implant device 260 is designed to extend over substantially the entire jaw bone of a patient and is used in cases where a patient has no existing tooth.

In FIG. 15, the total subperiosteal dental implant device 260 includes 8 single piece implant heads 250 extending from the frame 262, away from the jaw bone, when the frame 262 of the subperiosteal dental implant device 260 is superposed thereto. In FIG. 15, the implant heads 250 and are single-piece, i.e. they are not separated in head and receiving portions. It is appreciated that, in an alternative embodiment (not shown), head portions and the receiving portions can be provided as two distinct components of the implant heads 250 engageable together.

In view of the above, it will be understood that the subperiosteal dental implant device 160, 260 including one or more implant heads 150, 250 can be used to perform any conventional dental restorations including and without being limitative partial denture and full denture, which can include an overdenture, bridge, crown, and the like.

Figure 16A:
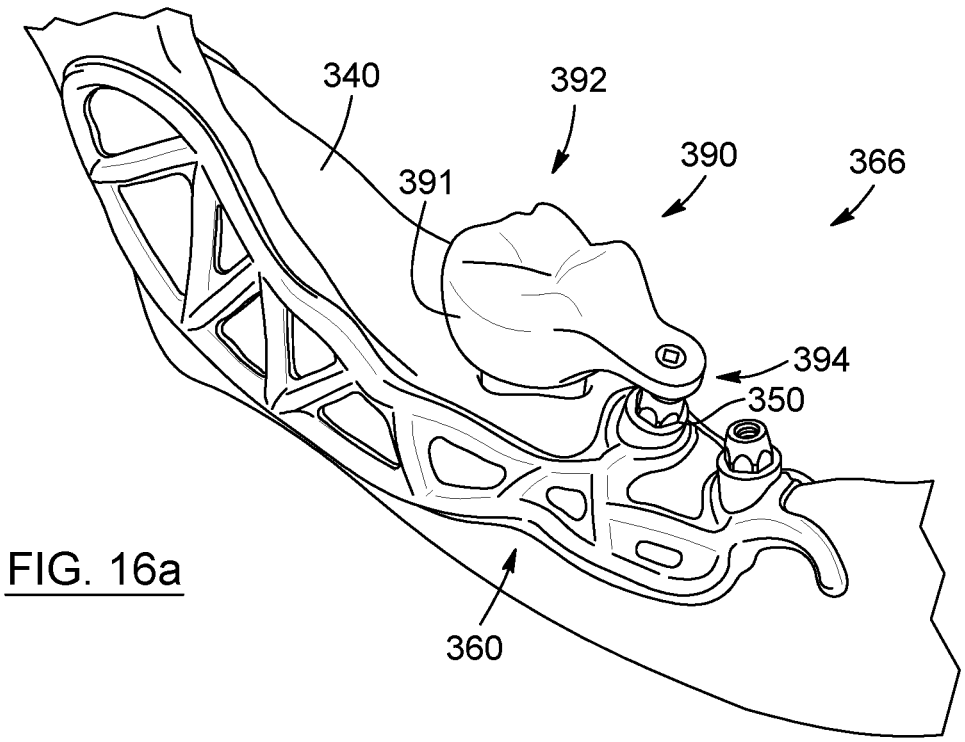
FIGS. 16a and 16b are respectively a perspective view of a partial subperiosteal dental implant device shown mounted to a jaw bone of a patient and with a positioning jig secured thereto; and the partial subperiosteal dental implant device shown mounted to a jaw bone of a patient, with the positioning jig removed therefrom.
Figure 16B:
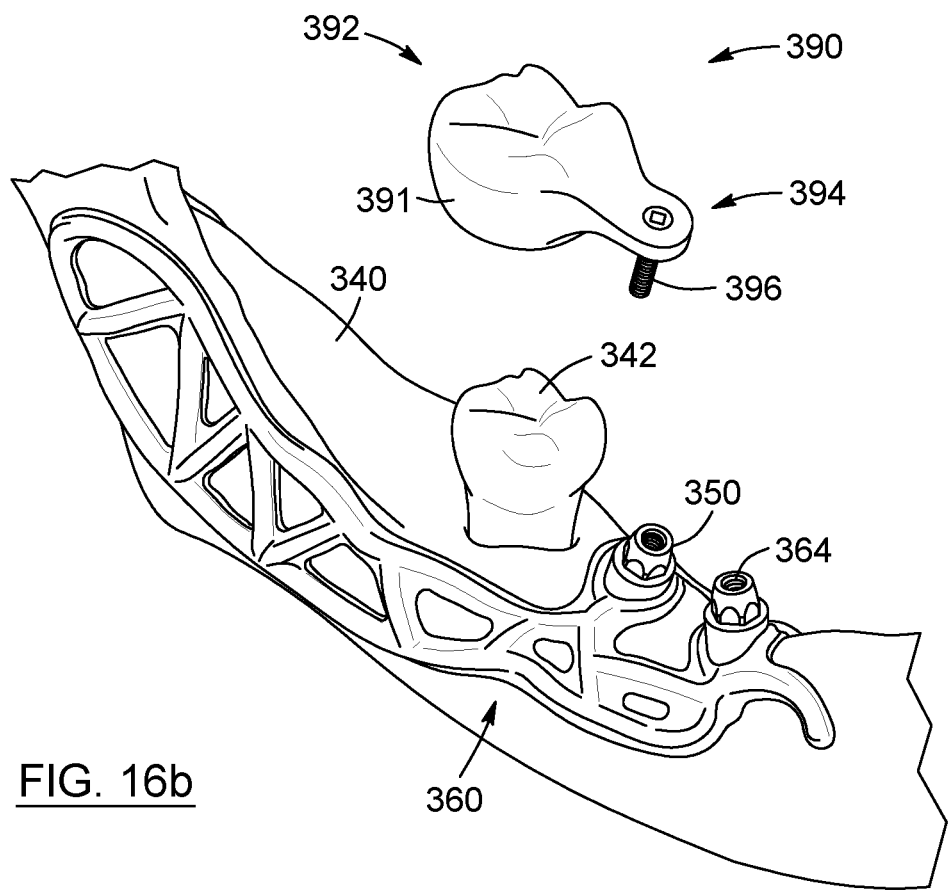

Now referring to FIGS. 16a and 16b, there is shown an alternative embodiment of the dental implant system 166 including the subperiosteal dental implant device 360, wherein similar features are numbered using the same reference numerals in the 300 series. In the embodiment shown in FIGS. 16a and 16b, the dental implant system 366 includes similar features and components as the dental implant system 166 described above in reference to FIG. 13 (without connectors 170), which do not need to be repeated herein. The dental implant system 366 further includes a positioning jig 390 removably engageable with the subperiosteal dental implant device 360 and at least one existing tooth 342 of the patient. More particularly, the positioning jig 390 provides a connection between the subperiosteal dental implant device 360 and at least one existing tooth 342 in order to help positioning the subperiosteal dental implant device 360 with respect to the jaw bone, before securing the subperiosteal dental implant device 360 to the jaw bone 340 of the patient. The positioning jig 390 is removed from the patient's mouth after the subperiosteal dental implant device 360 being secured to the jaw bone.

More particularly, the positioning jig 390 has a jig body 391 with a tooth engaging feature 392 engageable with the at least one existing tooth 342 of the patient. In an embodiment, the tooth engaging feature 392 can be custom-made to match an external profile of the at least one existing tooth 342 of the patient and therefore allow the tooth engaging feature 392 to be removably engageable to the at least one existing tooth 342 in a single position. More particularly, the tooth engaging feature 392 has a tooth facing surface which substantially conforms to at least a portion of an external surface of the respective one of the existing tooth 342 to which it is removably engageable. In an embodiment, the tooth engaging feature 392 of the positioning jig at least partially surrounds its respective existing tooth when engaged therewith.

The jig body 391 of the positioning jig 390 also has a frame engaging feature 394 removably engageable with the subperiosteal dental implant device 360 in a single position. In the embodiment shown, the frame engaging feature 394 of the positioning jig 390 includes a treaded end section 396 (e.g. a screw being part of the frame engaging feature 394) for engaging with the threaded socket 364 of a corresponding implant head 350. One skilled in the art will however understand that, in an alternative embodiment, the frame engaging feature 394 of the positioning jig 390 can be removably engageable to the subperiosteal dental implant device through other means or methods than the embodiment shown.

Thus, when the positioning jig 390 connects the subperiosteal dental implant device 360 and at least one existing tooth 342, the positioning jig 390 and the subperiosteal dental implant device 360 are positioned in a single position with respect to the jaw bone and the at least one existing tooth 342.

Even though, the embodiment of the positioning jig 390 includes only one tooth engaging feature 392 and only one frame engaging feature 394, it is appreciated that, in an alternative embodiment, the positioning jig 390 can include more than one tooth engaging feature 392 and/or more than one frame engaging feature 394.

As will be easily understood by one skilled in the art, for mounting the subperiosteal dental implant device 360 onto an exposed jaw bone with the dental implant system 366 including the positioning jig 390, the frame engaging feature 394 of the positioning jig 390 and the subperiosteal dental implant device 360 are engaged together. Then, the assembly including the positioning jig 390 and the subperiosteal dental implant device is superposed to the jaw bone in a manner such that the subperiosteal dental implant device 360 contacts the jaw bone 340 of the patient, with the tooth engaging feature 392 of the positioning jig 390 engaging the corresponding at least one existing tooth 342. As mentioned above, in an embodiment, the bone-facing surface of the subperiosteal dental implant device 360 substantially conforms to the external shape of the jaw bone of the patient. Engagement between the assembly including the positioning jig 390 and the subperiosteal dental implant device and the least one existing tooth 342 ensures that the subperiosteal dental implant device 360 is positioned in the predetermined single position. The subperiosteal dental implant device 360 can subsequently be secured to the jaw bone 340 of the patient. For instance, the subperiosteal dental implant device 360 can be secured by inserting one or more mechanical fasteners, such as fixation screws, into the subperiosteal dental implant device and the jaw bone. The positioning jig 390 can subsequently be detached from the subperiosteal dental implant device 360 and removed.

For example and without being limitative, in an embodiment where the frame engaging feature 394 of the positioning jig 390 includes a treaded end section 396 for engaging with the threaded socket 364 of a corresponding implant head 350, the positioning jig 390 can be engaged with and detached from the subperiosteal dental implant device 360 simply and respectively by threading and unthreading the treaded end section 396 from the threaded socket 364 of a corresponding implant head 350.

In the remaining of the description, for ease of description, reference number in the 100 series will only be used to refer to the components of the subperiosteal dental implant device 160 and dental implant system 166. However, it is appreciated that the described features also applies to the other embodiments of the subperiosteal dental implant device and dental implant system.

In view of the above, it will be understood that the implant head 150 to which a respective one of the replacement tooth or teeth 152 is directly or indirectly engaged can have a customized peripheral shape or can always be substantially cylindrical. As will be described in more details below, in an embodiment where the implant head 150 has a customized shape, the shape of the implant head 150 is determined based on the shape of the replacement tooth 152 engaged therewith. In an embodiment where the implant head 150 has circular shape, the shape of the replacement tooth 152 is rather adjusted to the shape of the implant head 150.

In an embodiment, the number of implant heads 150 can be inferior to the number of adjacent replacement teeth. For example and without being limitative, in an embodiment where a dental restoration includes three adjacent replacement teeth, only two of the replacement teeth can be engaged to a respective implant head 150 with the third replacement tooth being secured to at least one of the other replacement teeth.

As mentioned above, the method 10, the system 100, and the dental implant system 166 can be used for different types of restorations, such as maxillary and/or mandibular dental restorations.

Customized (or Patient-Specific) Implant Head

Now that embodiments of a subperiosteal dental implant device 160 and corresponding dental implant system 166 have been described in details above, an embodiment of a customized (patient-specific) implant head 150 to support directly or indirectly one or more of the replacement tooth and which can be used in a dental implant system 166 as described above or in different dental implant systems (not shown) or directly engaged with the patient's jaw will now be described in more details below.

As mentioned above, the implant head 150 is a component, which can be provided on a frame, such as and without being limitative the frame 162, to support directly or indirectly one or more of the replacement tooth 152. Each implant head 150 is configured to extend through the gum tissue 144 of the patient. The implant head 150 is also sized and shaped to fit with the replacement tooth 152 to which it is engageable. As mentioned above, the replacement tooth 152 can be selected form a library or catalog of tooth models.

With reference to FIGS. 17 and 19 (prior art), as mentioned above, it is known to use standard implant heads H, which are circular in shape and wherein a peripheral shape of a base section of the replacement tooth T must be shaped to fit with the standard implant head H. Thus, the base section of the replacement tooth typically have a circular shape, defined by the peripheral wall, in order to conform to the shape of the standard implant heads H at the junction thereof.

In contrast, with reference to FIGS. 18 and 20, in an embodiment, there is provided a customized (patient-specific) implant head 150 shaped and sized to fit with an irregular base section 154 of the replacement tooth 152, defined by its peripheral wall 156. In an embodiment, the irregular base section 154 of the replacement tooth 152 is non-circular and non-ovoidal.

More particularly, the customized implant head 150 includes a body 151 configured to at least partially extend through the gum tissue of the patient when mounted to the patient's jaw. The body 151 of the implant head 150 is engageable with the replacement tooth as it is known in the art. The body 151 has a peripheral wall 153 defining a peripheral shape of the customized implant head 150. When the customized implant head 150 and the replacement tooth 152 are engaged together, the peripheral wall 153 has a peripheral shape substantially matching a peripheral shape of the irregular base section of the replacement tooth 152 at their junction. More particularly, in an embodiment, the peripheral wall 156 defining the peripheral shape of the irregular base section 154 of the replacement tooth 152 and the peripheral wall 153 of the body 151 of the implant head 150 are in register at their junction Thus, in such an embodiment, the implant head 150 is sized and shaped to conform to the shape of the irregular base section 154 of the replacement tooth 152, rather than the replacement tooth T being shaped to fit with a standard implant head H (see FIGS. 17 and 19—prior art). In an embodiment, the customized implant head 150 extends between the frame of the subperiosteal implant 160 (or any other suitable implant base) and the gum line of the patient (i.e. the upper surface of the gum tissue 144). In an embodiment, the customized implant head 150 is integral with the dental implant device, such as the subperiosteal dental implant device 160. Therefore, the implant head 150 has a height which is adapted to the local thickness of the gum tissue 144 of the patient. In an embodiment, the junction between the replacement tooth 152 and the customized implant head 150 is in the vicinity of a gum line of the gum tissue when the replacement tooth 152 and the customized implant head 150 are mounted to the jaw of the patient, either slightly below, slightly above or substantially leveled with the gum line of the gum tissue.

Thus, the body 151 of the customized implant head 150 is custom-shaped and is at least partially derived from the peripheral shape of the irregular base section 154 of the peripheral wall 156 of the replacement tooth 152.

Figure 2:
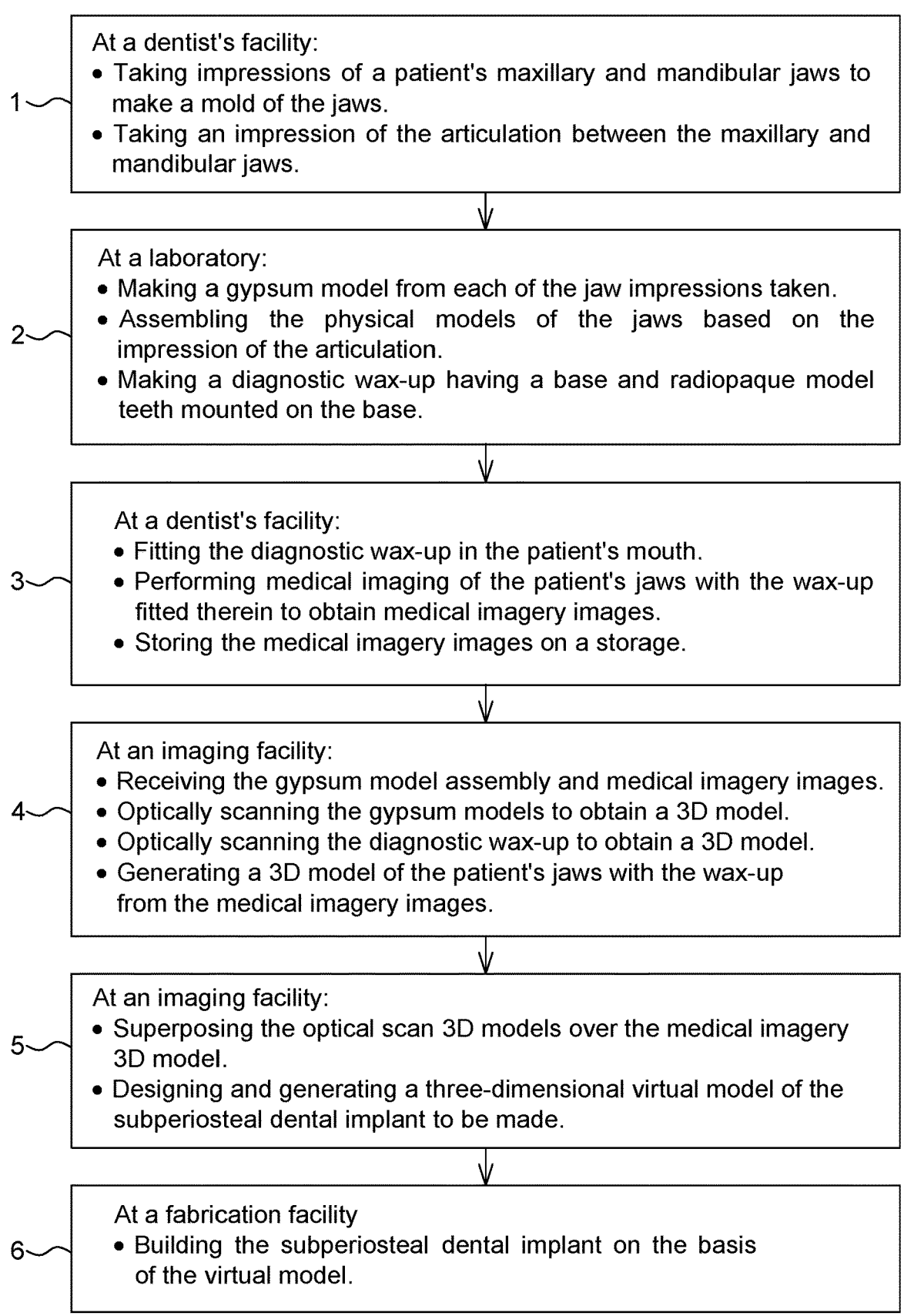
FIG. 2 is a bloc diagram showing steps of a process for making a subperiosteal dental implant device in accordance with an embodiment.
Figure 3:
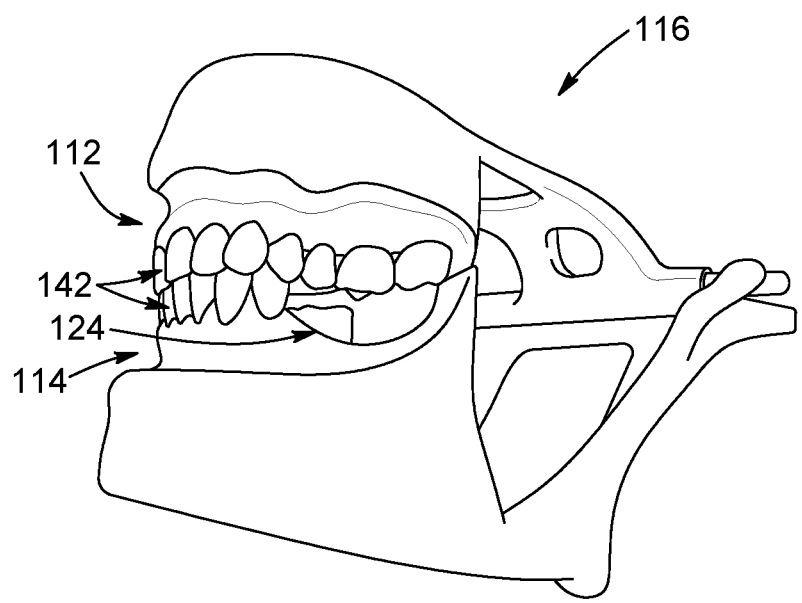
FIG. 3 is a perspective view of a model of a patient's jaw.
Figure 4:
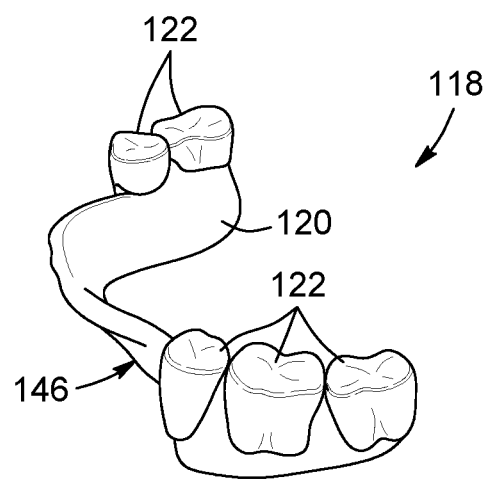
FIG. 4 is a perspective view of a diagnostic wax-up.
Figure 5:
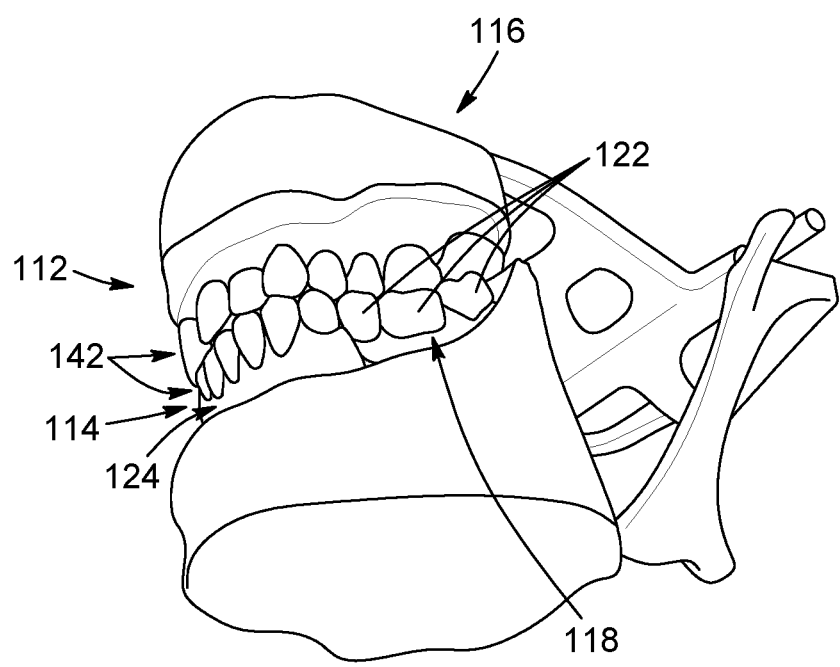
FIG. 5 is a perspective view of the model of FIG. 3, having mounted thereon the diagnostic wax-up of FIG. 4.

With reference to the above described method for generating a model of a subperiosteal dental implant device, in an embodiment, the local thickness of the gum tissue 144 of the patient can be defined during the step of superposing the 3D model 131 of the jaw(s) of the patient obtained from the medical imagery images, the 3D model 132 of the jaw of the patient obtained from the optical scan, and the 3D model 134 of the tooth models 122 of the diagnostic wax-up 118 models images (labelled as step 5b of the fifth step (step 5) of the general process with reference to FIGS. 1B, 2 and 12). In another embodiment, the thickness of the gum tissue can be approximated. Moreover, the implant head 150 is shaped, positioned and angled in accordance with the location of the corresponding replacement tooth 152 and the shape and configuration of the bone structure of the patient as can once again be defined in the above described step of superposing the 3D models 131, 132, 134, in accordance with an embodiment of the method for generating a model of a subperiosteal dental implant device.

In an embodiment, in order to conceive the customized implant head 150, a model of the replacement tooth 152 is selected in accordance with the bone structure, the already existing tooth/teeth (if any), the space available, and/or the gum tissue 144 of the patient. As mentioned above, in the base section, the peripheral shape of the replacement tooth is typically irregular. Thus, a tooth model of the replacement tooth 152 can be obtained to design, at least partially, the shape of the implant head 150 based on the shape of the replacement tooth. The tooth model can be a virtual tooth model. In an embodiment, the tooth model includes information about the peripheral shape of the peripheral wall of the replacement tooth 152, in the irregular base section thereof. Subsequently, the customized implant head 150 is designed using the tooth model. In an embodiment, a junction line between the irregular base section of the replacement tooth and the implant head, when engaged together, is determined. Determination of the junction line is performed using the model of the replacement tooth. When the junction line is determined, the peripheral shape of the peripheral wall of the replacement tooth at the junction line is determined using the tooth model. Using the determined peripheral shape of the peripheral wall of the replacement tooth at the junction line, at least a portion of the implant head is designed. More particularly, the peripheral wall of the body is designed such that its peripheral shape substantially matches the determined peripheral shape of the peripheral wall of the replacement tooth at the junction line. Thus, the peripheral shape of the implant head at the junction line with the replacement tooth is also irregular in shape.

In an embodiment where a virtual model of at least a section of the gum line of the gum tissue of the patient (the section being aligned with the replacement tooth) is available, the method can further include positioning the replacement tooth and the implant head with respect to the gum line and substantially aligning the junction line between the irregular base section of the replacement tooth and the implant head with the gum line. In an embodiment, the junction line is located either slightly below the gum line, substantially even with the gum line, or slightly above the gum line. In an embodiment, the position of the junction line can be selected by the dentist in charge of the implantation of the implant head(s) and the replacement tooth/teeth.

In an embodiment, the design of the implant head comprises extending the peripheral wall of the model of the replacement tooth 152, in the irregular base section, towards the section of the gum tissue 144 and the jaw bone 140, i.e. in a direction of a root of an existing tooth. The design of the peripheral shape of the peripheral wall of the implant head 150 can be based on the extension of the peripheral wall of the model of the replacement tooth 152 towards the section of the gum tissue 144 and the jaw bone 140. In other words, the peripheral shape of the implant head 150 corresponds to the extension of the peripheral wall of the replacement tooth model 152 at the junction line, with the peripheral wall of the implant head 150 being aligned with a base section of the peripheral wall of the replacement tooth model 152. In an embodiment, at the junction line, the peripheral wall of the implant head 150 is in register with the peripheral wall of the replacement tooth model 152 when engaged together.

More particularly, a peripheral shape of the virtual extension of the peripheral wall of the tooth model at the junction line can be determined and the peripheral shape of the peripheral wall of the body of the implant head can be shaped to be in register with the virtual extension of the peripheral wall of the tooth model at the junction line.

In an embodiment, the body of the implant head extending between a base section thereof, which can correspond to the junction with the dental implant device, such as the subperiosteal dental implant device, and the junction line with the replacement tooth can be substantially uniform in shape, i.e. the peripheral wall of the body can define a peripheral shape corresponding to the peripheral shape of the replacement tooth at the junction line from its base to the junction line.

In an embodiment, the conception of a customized (i.e. tooth specific) implant head 150 can be carried out subsequently to the conception of a base (such as the above described subperiosteal dental implant device 160).

For example and without being limitative, in an embodiment where the combined 3D model 136 is obtained by the superposition of the 3D models 131, 132, 134, with the subperiosteal dental implant device being designed based on the combined 3D model 136, the combined 3D model 136 can further be used for the conception of the customized implant head(s) 150. In such an embodiment, the model of the subperiosteal dental implant device 160 can be superposed to the combined 3D model 136 and the implant heads 150 associated to a respective one of the replacement teeth 152 can be designed by extending the base section of the peripheral walls of the replacement teeth 152 towards the model of the subperiosteal dental implant device 160 on the combined 3D model 136. Therefore, a shape of the peripheral wall of each one of the customized implant heads 150 substantially corresponds to the shape of the extension of the peripheral wall of the replacement tooth at the junction line. The peripheral walls of the customized implant heads 150 protrude from an upper surface of the subperiosteal dental implant device 160, towards the gum line. As mentioned above, the height of each one of the implant heads 150 can be selected based on the thickness of the gum tissue 144 at a position corresponding to the respective one of the implant heads 150.

In the above described embodiment, each one of the implant heads 150 is shaped to conform with the irregular peripheral shape of the replacement tooth 152, in the base section, to be mounted thereon (directly or indirectly through a connector 170) and, optionally, a relative position of the tooth 152 with respect to adjacent teeth and to the underlying gum tissue 144 and jaw bone 140.

One skilled in the art will easily understand that the above-described customized dental implant heads 150 can be provided on any dental implant device, such as a subperiosteal dental implant device, an elongated dental implant or the like, as well as to receive any suitable implant such as a replacement tooth, a dental implant bar, a dental bridge, etc.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention can be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A dental implant system comprising:
a subperiosteal dental implant device comprising:
a frame engageable to at least a section of a jaw bone of a patient, the frame at least partially conforming to an external shape of the section of the jaw bone of the patient;
an implant head configured to receive a corresponding one of at least one replacement tooth, the implant head extending from the frame and at least a portion of the implant head being integral with the frame; and
a positioning jig removably connectable between the subperiosteal dental implant device and at least one existing tooth of the patient, the positioning jig having a body with a tooth engaging feature engageable with the at least one existing tooth of the patient and a frame engaging feature removably engageable to the implant head.

2. The dental implant system of claim 1, wherein the at least one replacement tooth comprises a plurality of adjacent teeth secured to one another.

3. The dental implant system of claim 1, wherein the implant head comprises a threaded socket engageable by a connector, the connector comprising a threaded end for mating with the threaded socket of the implant head and a connecting head opposite the threaded end for connecting with the corresponding one of at least one replacement tooth.

4. The dental implant system of claim 1, wherein the frame has a bone-facing surface which substantially conforms to a section of the jaw bone of the patient to which the frame is superposed.

5. The dental implant system of claim 1, wherein the frame comprises a plurality of interconnected segments wherein at least some of the plurality of interconnected segments intersect with the implant head and the at least a portion of the implant head is mounted to the segments intersecting therewith.

6. The dental implant system of claim 1, wherein the corresponding one of at least one replacement tooth comprises a peripheral wall with an irregular base section and the implant head comprises a body engageable with the corresponding one of at least one replacement tooth, the body having a peripheral wall substantially matching a peripheral shape of the irregular base section of the peripheral wall of the corresponding one of at least one replacement tooth at a junction thereof.

7. A dental implant system for mounting at least one replacement tooth onto a jaw of a patient having at least one existing tooth, the dental implant system comprising:
a subperiosteal dental implant device having a frame superposable to a jaw bone of the jaw of the patient, the frame having a bone-facing surface at least partially conforming to an external shape of at least a section of the jaw bone of the patient; and
a positioning jig having a jig body with a tooth engaging feature engageable with at least one of the at least one existing tooth of the patient and a frame engaging feature removably engageable with the frame of the subperiosteal dental implant device, wherein when the tooth engaging feature of the positioning jig is engaged with a respective one of the at least one existing tooth of the patient, the frame engaging feature is engaged with the frame of the subperiosteal dental implant device, and the bone-facing surface of the frame of the subperiosteal dental implant device is superposed to the jaw bone of the patient, the subperiosteal dental implant device is positioned in a single predetermined position with respect to the jaw bone of the patient.

8. The dental implant system of claim 7, wherein the at least one replacement tooth comprises a plurality of adjacent teeth secured to one another.

9. The dental implant system of claim 7, wherein the subperiosteal dental implant device further comprises at least a portion of an implant head configured to receive a corresponding one of the at least one replacement tooth, the at least a portion of the implant head being mounted to and extending from the frame.

10. The dental implant system of claim 9, wherein the at least a portion of the implant head is integral with the frame.

11. The dental implant system of claim 9, wherein the frame engaging feature is removably securable to the at least a portion of the implant head.

12. The dental implant system of claim 9, wherein the at least a portion of the implant head of the subperiosteal dental implant device comprises a threaded socket and the frame engaging feature is removably engageable with the threaded socket of the at least a portion of the implant head.

13. The dental implant system of claim 9, wherein the at least a portion of the implant head comprises a body engageable with the corresponding one of the at least one replacement tooth and the corresponding one of the at least one replacement tooth comprises a peripheral wall with an irregular base section, the body of the at least a portion of the implant head having a peripheral wall substantially matching a peripheral shape of the irregular base section of the peripheral wall of the corresponding one of the at least one replacement tooth at a junction thereof.

14. The dental implant system of claim 9, wherein the tooth engaging feature of the positioning jig at least partially surrounds the respective one of the at least one existing tooth of the patient when engaged therewith.

15. The dental implant system of claim 9, wherein the tooth engaging feature comprises a tooth facing surface, the tooth facing surface substantially conforming to at least a portion of an external surface of the respective one of the at least one existing tooth of the patient.

16. A method for mounting a subperiosteal dental implant device to a jaw bone of a patient, the method comprising the steps of:
   providing the dental implant system of claim 9;
   engaging the frame engaging feature of the positioning jig with the frame of the subperiosteal dental implant device;
   superposing the bone-facing surface of the frame to the jaw bone of the patient with the bone-facing surface substantially conforming to the jaw bone of the patient to which it is superposed;
   engaging the tooth engaging feature of the positioning jig with the respective one of the at least one existing tooth of the patient;
   securing the subperiosteal dental implant device to the jaw bone of the patient; and
   disengaging the tooth engaging feature of the positioning jig from the respective one of the at least one existing tooth of the patient and the frame engaging feature from the frame of the subperiosteal dental implant device and removing the positioning jig.

17. A dental implant system comprising:
   a replacement tooth having an outwardly-facing peripheral wall with an irregular base section, the irregular base section having a non-circular and non-ovoidal cross-section; and
   a subperiosteal dental implant device comprising:
      a frame engageable to at least a section of a jaw bone of a patient, the frame at least partially conforming to an external shape of the section of the jaw bone of the patient; and
      an implant head having a body extending from the frame with at least a portion of the implant head being integral with the frame, the implant head having a treaded socket extending therethrough from a free end thereof, the body being engageable with the replacement tooth and having an outer peripheral wall, the body having a non-circular and non-ovoidal cross-section substantially matching the non-circular and non-ovoidal cross-section of the irregular base section of the replacement tooth at a junction thereof.

18. The dental implant system of claim 17, wherein the non-circular and non-ovoidal cross-section of the body of the implant head is in register with the non-circular and non-ovoidal cross-section of the irregular base section of the replacement tooth at the junction thereof.

* * * * *